(12) United States Patent
Korosec et al.

(10) Patent No.: US 10,405,772 B2
(45) Date of Patent: Sep. 10, 2019

(54) MAGNETIC RESONANCE ANGIOGRAPHY AND VENOGRAPHY

(71) Applicants: Wisconsin Alumni Research Foundation, Inc., Madison, WI (US); General Electric Company, Schenectady, NY (US)

(72) Inventors: Frank R. Korosec, Middleton, WI (US); James H. Holmes, Madison, WI (US); Daniel V. Litwiller, Rochester, MN (US); Mahdi Salmani Rahimi, Madison, WI (US)

(73) Assignees: WISCONSIN ALUMNI RESEARCH FOUNDATION, INC., Madison, WI (US); GENERAL ELECTRIC COMPANY, Schenectady, NY (US)

( * ) Notice: Subject to any disclaimer, the term of this patent is extended or adjusted under 35 U.S.C. 154(b) by 1153 days.

(21) Appl. No.: 13/622,251

(22) Filed: Sep. 18, 2012

(65) Prior Publication Data
US 2014/0081123 A1 Mar. 20, 2014

(51) Int. Cl.
*A61B 5/00* (2006.01)
*A61B 5/055* (2006.01)
(Continued)

(52) U.S. Cl.
CPC ............ *A61B 5/055* (2013.01); *A61B 5/7285* (2013.01); *G01R 33/5635* (2013.01);
(Continued)

(58) Field of Classification Search
CPC ......... A61B 5/055; A61B 5/05; A61B 5/7285; G01R 33/20; G01R 33/567
See application file for complete search history.

(56) References Cited

U.S. PATENT DOCUMENTS 6,320,377 B1 * 11/2001 Miyazaki ............... A61B 5/055
324/306
7,412,277 B1 * 8/2008 Saranathan ........ G01R 33/4835
600/410
(Continued)

OTHER PUBLICATIONS

Edelman et al., "Quiescent-Interval Single-Shot Unenhanced Magnetic Resonance Angiography of Peripheral Vascular Disease: Technical Considerations and Clinical Feasibility", Magn Reson Med, Apr. 2010, vol. 63 (4), 19 pages.

*Primary Examiner* — Tse W Chen
*Assistant Examiner* — Joanne M Hoffman
(74) *Attorney, Agent, or Firm* — Shumaker & Sieffert, P.A.

(57) ABSTRACT

Techniques and systems for non-contrast enhanced magnetic resonance angiography and venography (MRAV) are described. For example, within one cardiac cycle of a subject, a single shot acquisition of non-suppressed arterial MR signals and a single shot acquisition of non-suppressed venous MR signals are employed. Radio frequency (RF) saturation pulses may be applied to one or more slabs such that MR signals indicative of venous blood that flows into the arterial imaging slice are substantially suppressed and MR signals indicative of arterial blood that flows in the venous imaging slice are substantially suppressed. The RF saturation pulses and the single shot acquisitions may be timed such that one or more of the single shot acquisitions occur during substantially steady state inflow of blood into the respective imaging slice. In this manner, k-space data may be acquired from arterial specific and venous specific imaging slices occurring within a single cardiac cycle.

22 Claims, 13 Drawing Sheets

(51) Int. Cl.
*G01R 33/563* (2006.01)
*A61B 5/026* (2006.01)
*A61B 5/0456* (2006.01)
*G01R 33/483* (2006.01)

(52) U.S. Cl.
CPC ........... *A61B 5/0263* (2013.01); *A61B 5/0456* (2013.01); *G01R 33/4838* (2013.01)

(56) References Cited

U.S. PATENT DOCUMENTS

| | | | |
|---|---|---|---|
| 2010/0268062 A1 | 10/2010 | Edelman | |
| 2011/0137146 A1* | 6/2011 | Edelman | G01R 33/5635 600/410 |
| 2011/0275926 A1* | 11/2011 | Du | G01R 33/5635 600/410 |

* cited by examiner

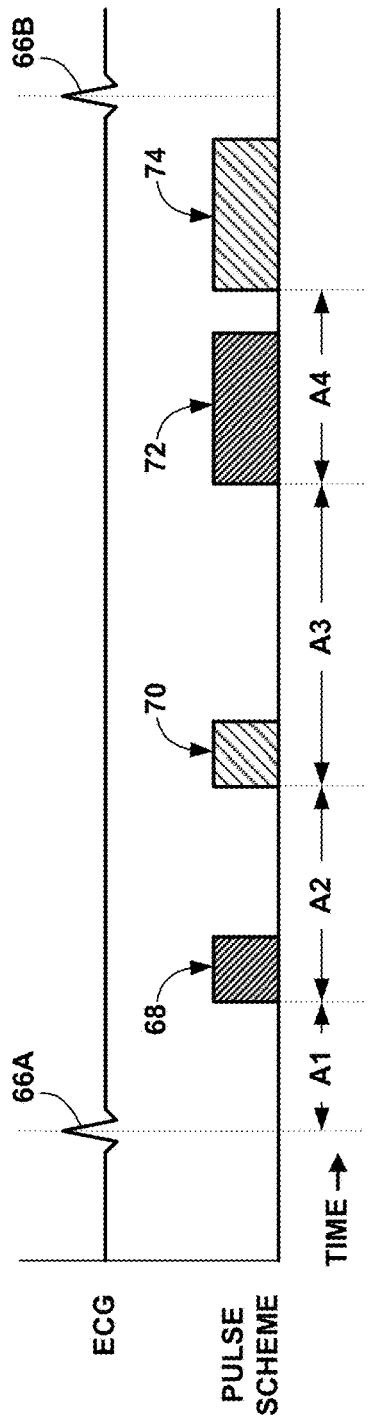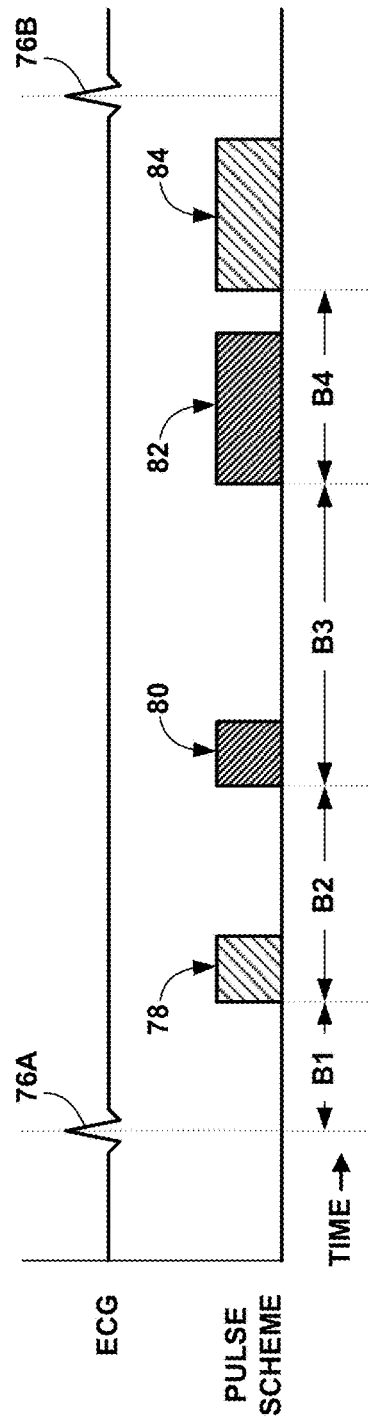

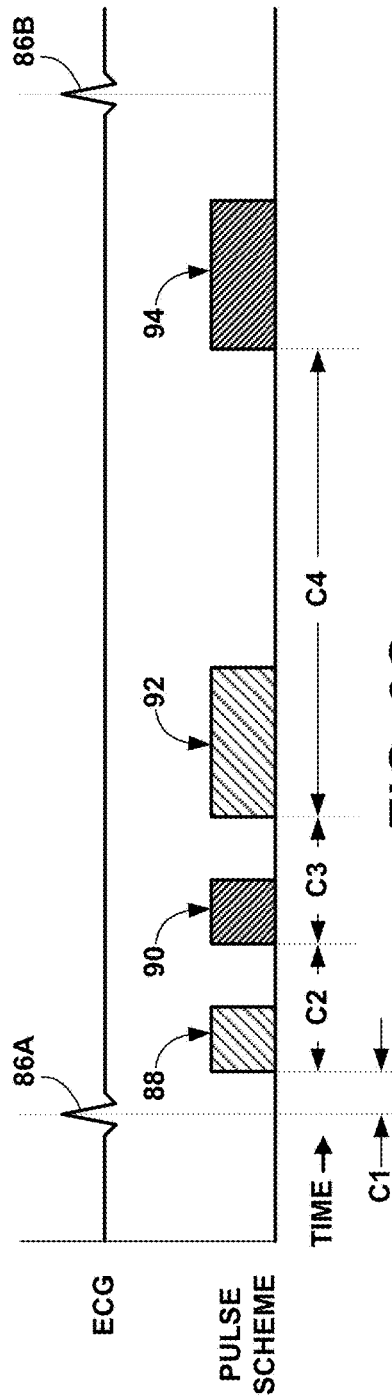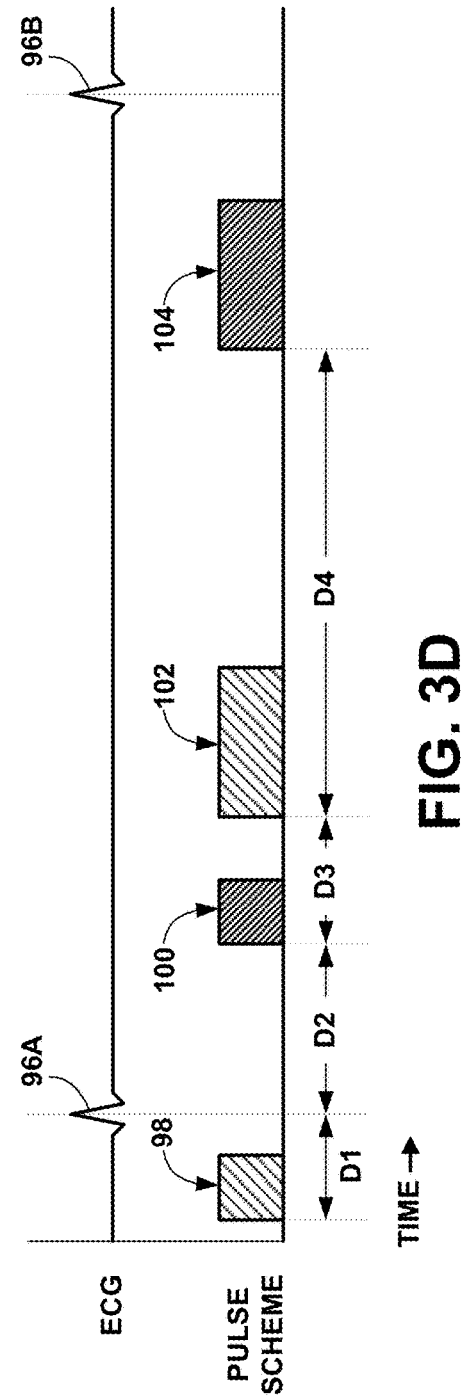

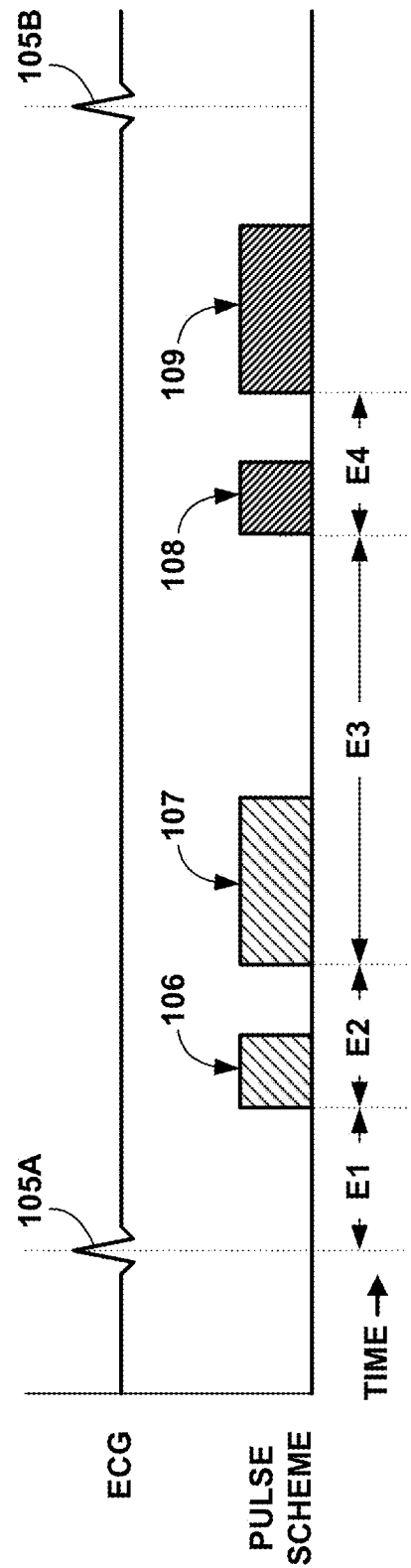

MAGNETIC RESONANCE ANGIOGRAPHY AND VENOGRAPHY

STATEMENT REGARDING FEDERALLY SPONSORED RESEARCH

This invention was made with government support under EB006882 awarded by the National Institutes of Health. The government has certain rights in the invention.

TECHNICAL FIELD

The invention relates to magnetic resonance imaging and systems, and, more particularly, to techniques and systems for non-contrast enhanced magnetic resonance angiography and venography.

BACKGROUND

When a substance such as human tissue is subjected to a uniform magnetic field (polarizing field $B_0$), the individual magnetic moments of the nuclei in the tissue attempt to align with this polarizing field, but precess about it in random order at their characteristic Larmor frequency. If the substance, or tissue, is subjected to a magnetic field (excitation field $B_1$) that is in the x-y plane and that is near the Larmor frequency, the net aligned moment, $M_z$, may be rotated, or "tipped", into the x-y plane to produce a net transverse magnetic moment $M_{xy}$. A signal is emitted by the excited nuclei or "spins", after the excitation signal $B_1$ is terminated, and this signal may be received and processed to form an image.

When utilizing these "MR" signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received MR signals are digitized and processed to reconstruct the image using one of many well known reconstruction techniques.

The measurement cycle used to acquire each MR signal is performed under the direction of a pulse sequence produced by a pulse sequencer. Clinically available MRI systems store a library of such pulse sequences that can be prescribed to meet the needs of many different clinical applications. Research MRI systems include a library of clinically proven pulse sequences and they also enable the development of new pulse sequences.

Magnetic resonance angiography ("MRA") uses the magnetic resonance phenomenon to produce images of the human vasculature. To enhance the diagnostic capability of MRA, some alternative techniques are employed. For example, a contrast agent such as gadolinium can be injected into the patient prior to the MRA scan. This contrast enhanced ("CE") MRA method requires that acquisition of the central k-space views must occur at the moment the bolus of contrast agent is flowing through the vasculature of interest. If the central lines of k-space are acquired prior to the arrival of contrast, severe image artifacts can limit the diagnostic information in the image. Alternatively, arterial images acquired after the passage of the peak arterial contrast are sometimes obscured by the enhancement of veins. The short separation time between arterial and venous enhancement dictates the use of acquisition sequences of either low spatial resolution or very short repetition times ("TR"). Short TR acquisition sequences severely limit the signal-to-noise ratio ("SNR") of the acquired images relative to those exams in which a longer TR is employed. The rapid acquisitions required by first pass CE-MRA methods thus impose an upper limit on either spatial or temporal resolution. In addition, some patients may be sensitive to contrast agents necessary in CE-MRA methods. Similar MRA techniques may be used for Magnetic resonance venography ("MRV") to image veins.

SUMMARY

Generally, this disclosure describes techniques and systems for non-contrast enhanced magnetic resonance angiography and venography (MRAV). For example, within one cardiac cycle of a subject, a single shot acquisition of non-suppressed arterial MR signals and a single shot acquisition of non-suppressed venous MR signals occurs based on the employed pulse sequence. Radio frequency (RF) saturation pulses may be applied to one or more slabs such that MR signals indicative of venous blood that flows into the arterial imaging slice are substantially suppressed and MR signals indicative of arterial blood that flows in the venous imaging slice are substantially suppressed. The RF saturation pulses and the single shot acquisitions may be timed such that one or more of the single shot acquisitions occur during substantially steady state inflow of blood into the respective imaging slice. In this manner, k-space data, or any other types of data, may be acquired from arterial specific and venous specific imaging slices occurring within a single cardiac cycle.

In other examples, the techniques described herein may not be limited to arterial and venous acquisition within a single cardiac cycle. Instead, the techniques may also be applied to two or more arteries, two or more veins, or any combination of at least one artery and at least one vein. For example, blood may be selectively imaged from two arteries with generally opposing flow directions. In this manner, the MRAV technique may be used to selectively image blood from two or more vessels.

In one example, the disclosure describes a method including acquiring a signal indicative of a start of a cardiac cycle of a subject and performing, by one or more processors, a pulse sequence that directs a magnetic resonance imaging (MRI) system, during the cardiac cycle, to apply one or more radio frequency (RF) saturation pulses to one or more slabs such that magnetic resonance (MR) signals indicative of blood that flows into one or more imaging slices are substantially suppressed, acquire first data from the subject following the application of one or more first RF excitation pulses, wherein the first data is indicative of MR signals from blood of a first vessel and substantially suppressed MR signals from blood of a second vessel, and acquire second data from the subject following the application of one or more second RF excitation pulses, wherein the second data is indicative of MR signals from blood of the second vessel and substantially suppressed MR signals from blood of the first vessel. The method also comprises reconstructing, from the acquired first data, a first image that represents at least a portion of the first vessel the subject and reconstructing, from the acquired second data, a second image that represents at least a portion of the second vessel of the subject.

In another example, the disclosure describes a computing system including one or more processors configured to acquire a signal indicative of a start of a cardiac cycle of a subject and perform a pulse sequence that directs a magnetic resonance imaging (MRI) system, during the cardiac cycle, to apply one or more radio frequency (RF) saturation pulses to one or more slabs such that magnetic resonance (MR)

signals indicative of blood that flows into one or more imaging slices are substantially suppressed, acquire first data from the subject following the application of one or more first RF excitation pulses, wherein the first data is indicative of MR signals from blood of a first vessel and substantially suppressed MR signals from blood of a second vessel, and acquire second data from the subject following the application of one or more second RF excitation pulses, wherein the second data is indicative of MR signals from blood of the second vessel and substantially suppressed MR signals from blood of the first vessel. The one or more processors may also be configured to reconstruct, from the acquired first data, a first image that represents at least a portion of the first vessel of the subject and reconstruct, from the acquired second data, a second image that represents at least a portion of the second vessel of the subject.

In another example, the disclosure describes a computer-readable storage medium comprising instructions that cause one or more processors to acquire a signal indicative of a start of a cardiac cycle of a subject and perform a pulse sequence that directs a magnetic resonance imaging (MRI) system, during the cardiac cycle, to apply one or more radio frequency (RF) saturation pulses to one or more slabs such that magnetic resonance (MR) signals indicative of blood that flows into one or more imaging slices are substantially suppressed, acquire first data from the subject following the application of one or more first RF excitation pulses, wherein the first data is indicative of MR signals from blood of a first vessel and substantially suppressed MR signals from blood of a second vessel, and acquire second data from the subject following the application of one or more second RF excitation pulses, wherein the second data is indicative of MR signals from blood of the second vessel and substantially suppressed MR signals from blood of the first vessel. The computer-readable storage medium comprising instructions that cause one or more processors to reconstruct, from the acquired first data, a first image that represents at least a portion of the first vessel of the subject and reconstruct, from the acquired second data, a second image that represents at least a portion of the second vessel of the subject.

The details of one or more examples are set forth in the accompanying drawings and the description below. Other features, objects, and advantages will be apparent from the description and drawings, and from the claims.

BRIEF DESCRIPTION OF DRAWINGS

FIGS. 3A-3E are conceptual timing diagrams of example radio frequency (RF) pulse schemes for MRAV.

DETAILED DESCRIPTION

Figure 1:
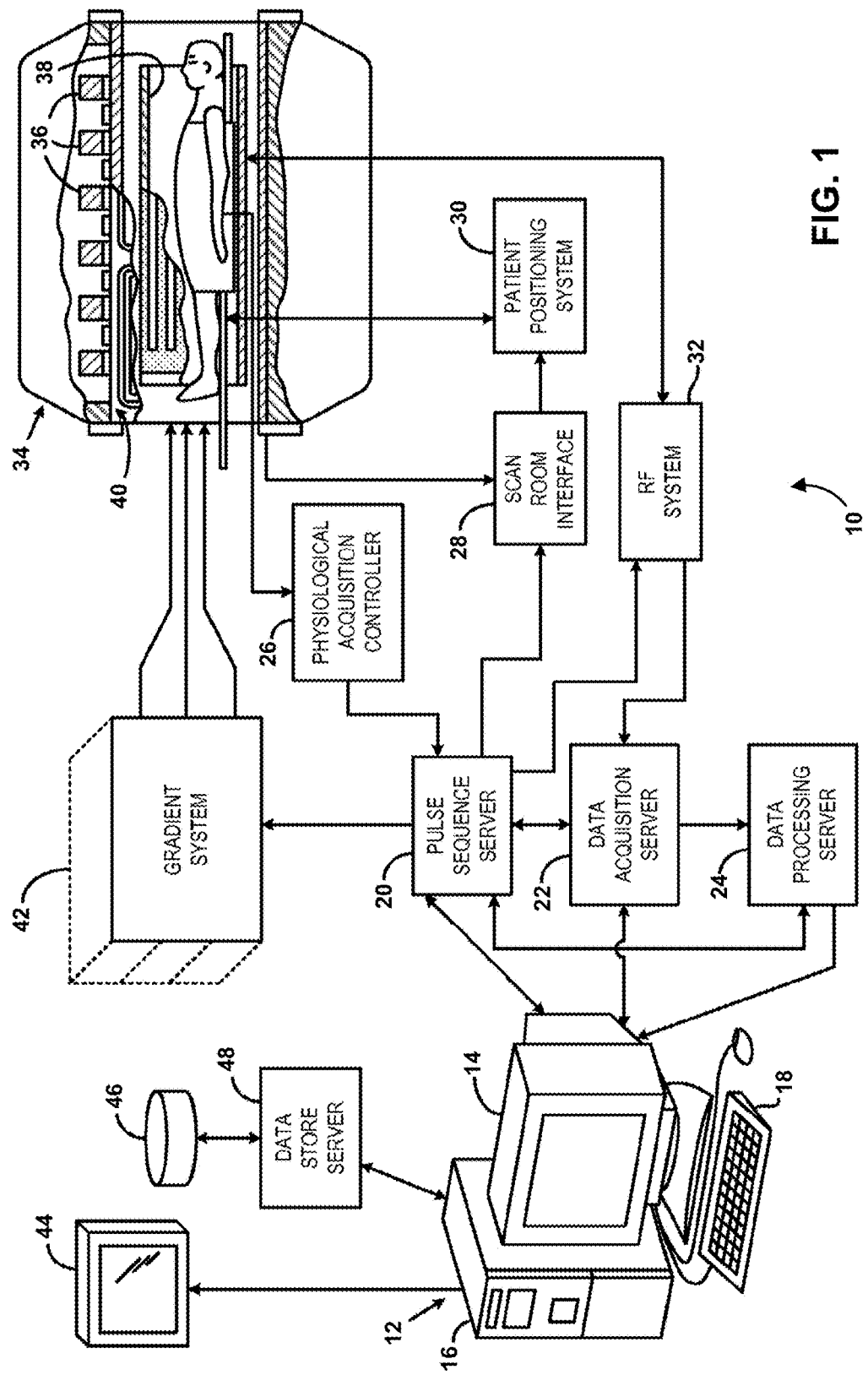
FIG. 1 is a block diagram of an example magnetic resonance imaging (MRI) system configured to employ magnetic resonance angiography and venography (MRAV) as described herein.

This disclosure describes techniques, systems, and devices, for non-contrast enhanced magnetic resonance angiography and venography (MRAV). Acquiring diagnostic images of the vasculature, particularly distal vasculature, of a patient can be difficult and time consuming. Some MRI methods employ contrast enhanced (CE) techniques to improve the diagnostic quality of the images of subject vasculature. Contrast agents, such as gadolinium, may be injected into the subject prior to the imaging scan. However, the scan must track the bolus of contrast agent through the vasculature in order for the contrast agent to improve the contrast of the blood with respect to other adjacent tissues in the subject. If the bolus can be tracked, the contrast enhanced techniques still result in relatively short window for image acquisition. In addition, some contrast agents can produce complications such as discomfort, pain, renal impairment, and even disorders such as nephrogenic systemic fibrosis (i.e., fibrosis of skin, joints, eyes, and internal organs).

Due to these drawbacks, other non-contrast enhanced MR based imaging techniques have been explored. For example, two-dimensional time of flight (2DTOF) is one acquisition method that has been developed for magnetic resonance angiography (MRA) of the lower extremities. However, the 2DTOF imaging technique can be too long for many subjects to tolerate, is sensitive to subject motion during imaging, and suffers from flow artifacts within horizontally oriented vessel segments. As another example, the quiescent-interval single shot (QISS) MRA technique has been used to evaluate arterial vasculature. However, the QISS MRA technique does not provide any venous imaging because the venous blood signals are suppressed to enable arterial imaging. Furthermore, the QISS MRA technique may have trouble visualizing arteries that follow tortuous pathways, or run counter to the slice acquisition order.

As described herein, non-contrast enhanced MRAV techniques include a variety of different pulse sequences that enable, within a single cardiac cycle, the acquisition of arterial specific magnetic resonance (MR) signals in one imaging slice and venous specific MR signals in another imaging slice. The MRAV techniques may include preparatory radio frequency (RF) saturation pulses applied to one or more slabs to selectively suppress MR signals from blood flowing into a selected imaging slice. For example, the RF saturation pulses may be selected and timed such that MR signals from venous blood are suppressed in the arterial specific imaging slice and MR signals from arterial blood are suppressed in the venous specific imaging slice.

In this manner, a pulse sequence for acquiring k-space data of both an arterial enhanced imaging slice and a venous enhanced imaging slice may include a scheme of at least different sets of RF pulses. An arterial preparatory set of RF pulses may include one or more RF saturation pulses selected to suppress venous blood MR signals. An arterial acquisition set of RF pulses may include one or more RF excitation pulses selected to allow acquisition of k-space data indicative of arterial blood MR signals and the suppressed venous blood MR signals. A venous preparatory set of RF pulses may include one or more RF saturation pulses selected to suppress arterial blood MR signals. A venous acquisition set of RF pulses may include one or more RF excitation pulses selected to allow acquisition of k-space data indicative of venous blood MR signals and the suppressed arterial blood MR signals. In other examples, fewer RF pulse sets may be used with multiplexed slab-selective suppression and/or multiplexed acquisition.

Typically, the arterial preparatory set of RF pulses would be applied prior to the arterial acquisition set of RF pulses, and the venous preparatory set of RF pulses would be applied prior to the venous acquisition set of RF pulses. However, the order of each of these sets of RF pulses may be varied and/or timed within the cardiac cycle to achieve desired suppression of MR signals and acquisition of MR signals during desired blood flow velocities. For example, both preparatory sets of RF pulses may be applied to the subject prior to the application of any acquisition sets of RF pulses. To provide maximum signal enhancement, the arterial acquisition set of RF pulses may be timed near the end of a cardiac cycle to coincide with relatively steady inflow of arterial blood into the arterial imaging slice. The spatial positioning for the applied RF saturation pulses (e.g., the saturation bands) and the applied RF excitation pulses (e.g., the imaging slices) may also be varied to achieve desired suppression of undesired MR signals, background artifacts, and the like.

The MRAV techniques described herein may provide images of the arterial vasculature and venous vasculature in a relatively short duration of time while maintaining discrimination of the desired arteries or veins. The MRAV techniques described herein may also be substantially insensitive to blood flow velocities and relatively insensitive to patient motion and other imaging artifacts. In addition, the MRAV techniques described herein may allow for the acquisition of directionally-opposed arterial and venous signals within a single cardiac cycle (i.e., without a scan-time penalty compared to angiography only techniques). In some examples, the MRAV techniques may also improve the diagnostic utility of inflow imaging techniques by allowing for the visualization of venous anatomy and tortuous vessel pathways that may run counter to the imaging slice acquisition order. Although the MRAV techniques described herein may be particularly suited for relatively long vessels within the legs or arms, these techniques may be applied to any anatomical location of a subject. The MRAV techniques may be described, in some examples, as a preparation time single shot magnetic resonance angiography and venography due to the use of preparation intervals for single shot acquisitions for each of the arterial and venous imaging slices.

The MRAV technique is generally described herein with respect to acquiring MR signals from arterial blood and venous blood within a single cardiac cycle. However, the MRAV technique is not so limited. For example, the technique may also be configured such that blood from more than one artery and/or more than one vein can be imaged within a single cardiac cycle. In other examples, the technique may be used to image blood from any types of vessels with generally opposing direction of blood flow. For example, the technique may be used to, within a single cardiac cycle, acquire data indicative of blood from one artery and acquire data indicative of blood from another artery. In this manner, the MRAV technique described herein may be used to selectively image blood from two or more vessels, regardless of the blood being arterial blood or venous blood.

A subject or patient described herein may generally refer to a human. However, in other examples, the subject or patient may be a non-human mammal or other animal that may respond to MRAV techniques.

FIG. 1 is a block diagram of an example magnetic resonance imaging (MRI) system 10 configured to employ MRAV as described herein. The technique of MRAV may be typically employed in an MRI system. The MRI system may include a workstation 12 having a display 14 and a keyboard 18. The workstation 12 may include a processor 16 that is a programmable machine running an operating system that may or may not be commercially available. Workstation 12 provides the operator interface that enables scan prescriptions to be entered into MRI system 10. Workstation 12 may be coupled to, for example, four servers: a pulse sequence server 20; a data acquisition server 22; a data processing server 24, and a data store server 48. Each of servers 20, 22, 24, and 48 may include one or more processors configured to perform the functions ascribed to each server herein. Workstation 12 and each of servers 20, 22, 24, and 48 are connected to communicate with each other. In other examples, one or more servers may perform the functionality of each of servers 20, 22, 24, and 48. In one example, workstation 12 may include and/or be configured to perform the functions of servers 20, 22, 24, and 48.

Pulse sequence server 20 may be configured to function in response to instructions downloaded from workstation 12 to operate a gradient system 42 and a radio frequency (RF) system 32. Pulse sequence server 20 may include one or more processors configured to perform the functions described herein with regard to pulse sequences for MRAV. Gradient waveforms to perform the prescribed scan are produced and applied to gradient system 42 configured to excite gradient coils in an assembly 40 to produce the magnetic field gradients $G_x$, $G_y$, and $G_x$ used for position encoding MR signals. Gradient coil assembly 40 may form part of a magnet assembly 34 that includes a polarizing magnet 36 and a whole-body RF coil 38.

RF excitation waveforms may be applied to RF coil 38 by RF system 32 to perform the prescribed magnetic resonance pulse sequence (e.g., a pulse sequence selected for MRAV). Responsive MR signals detected by RF coil 38 or a separate local coil (not shown in FIG. 1) may be received by RF system 32, amplified, demodulated, filtered and digitized under direction of commands produced by the pulse sequence server 20. RF system 32 may include an RF transmitter for producing a wide variety of RF pulses used in MR pulse sequences. The RF transmitter is responsive to the scan prescription and direction from the pulse sequence server 20 to produce RF pulses of the desired frequency, phase and pulse amplitude waveform. The generated RF pulses may be applied to the whole body RF coil 38 or to one or more local coils or coil arrays (not shown in FIG. 1).

RF system 32 may also include one or more RF receiver channels. Each RF receiver channel may include an RF amplifier that amplifies the MR signal received by the coil to which it is connected and a detector that detects and digitizes the I and Q quadrature components of the received MR signal. The magnitude of the received MR signal may thus be determined at any sampled point by the square root of the sum of the squares of the I and Q components:

$$M=\sqrt{I^2+Q^2},$$

and the phase of the received MR signal may also be determined:

$$\phi = \tan^{-1}\left(\frac{Q}{I}\right).$$

Pulse sequence server 20 may also be configured to optionally receive patient data from a physiological acquisition controller 26. Controller 26 may be configured to receive signals from a number of different sensors connected to the patient, such as electrocardiogram (ECG) signals from electrodes or respiratory signals from a bellows. Such signals are typically used by the pulse sequence server 20 to synchronize, or "gate", the performance of the scan with the subject's respiration or heart beat. For example, pulse sequence server 20 may identify R-waves within a received ECG signal Pulse sequence server 20 may also be connected to a scan room interface circuit 28 configured to receive signals from various sensors associated with the condition of the patient and the magnet system. It is also through the scan room interface circuit 28 that a patient positioning system 30 may receive commands to move the patient to desired positions during the scan.

The digitized MR signal samples produced by RF system 32 may be received by data acquisition server 22. Data acquisition server 22 may operate in response to instructions downloaded from workstation 12 to receive the real-time MR data and provide buffer storage such that no data is lost by data overrun. In some scans, data acquisition server 22 does little more than pass the acquired MR data to the data processor server 24. However, in scans that require information derived from acquired MR data to control the further performance of the scan, data acquisition server 22 may be programmed to produce such information and convey it to pulse sequence server 20. For example, during prescans, MR data is acquired and used to calibrate the pulse sequence performed by pulse sequence server 20. Also, navigator signals may be acquired during a scan and used to adjust RF or gradient system operating parameters or to control the view order in which k-space is sampled. In such examples, data acquisition server 22 may be configured to acquire MR data and processes the MR data in real-time to produce information that is used to control the scan.

Data processing server 24 may be configured to receive MR data from data acquisition server 22, and processes, the MR data in accordance with instructions downloaded from workstation 12. Such processing may include, for example: Fourier transformation of raw k-space MR data to produce two or three-dimensional images; the application of filters to a reconstructed image; the performance of a backprojection image reconstruction of acquired MR data; the calculation of functional MR images; and the calculation of motion or flow images.

Images reconstructed by data processing server 24 are conveyed back to the workstation 12 where they are stored. Real-time images may be stored in a data base memory cache (not shown) from which they may be output to operator display 14 or a display 44 that is located near the magnet assembly 34 for use by attending physicians. Batch mode images or selected real time images may be stored in a host database on disc storage 46. When such images have been reconstructed and transferred to storage, data processing server 24 may be configured to notify data store server 48 on workstation 12. Workstation 12 may be used by an operator to archive the images, produce films, or send the images via a network to other facilities.

Processors that may perform the functions described herein may include any one or more of a microprocessor, a controller, a digital signal processor (DSP), an application specific integrated circuit (ASIC), a field-programmable gate array (FPGA), or equivalent discrete or analog logic circuitry. In some examples, one or more processors may include multiple components, such as any combination of one or more microprocessors, one or more controllers, one or more DSPs, one or more ASICs, or one or more FPGAs, as well as other discrete or integrated logic circuitry. The functions attributed to any servers, processors, or modules herein may be embodied as software, firmware, hardware or any combination thereof.

Any data storage devices or memory (e.g., data store server 48) may include any volatile, non-volatile, magnetic, optical, or electrical storage media, such as a random access memory (RAM), read-only memory (ROM), non-volatile RAM (NVRAM), electrically-erasable programmable ROM (EEPROM), flash memory, or any other digital or analog storage media.

As will be described herein, MRI system 10 (e.g., a computer system) may be configured to perform any of the MRAV techniques herein. For example, pulse sequence server 20 may be configured to cause RF system 32 to apply selected RF signals to selected slices, slabs, or bands in order to suppress certain MR signals (e.g., suppress arterial and/or venous blood inflowing to an imaging slice and/or other background artifacts) and or acquire desired MR signals from an imaging slice.

Figure 2:
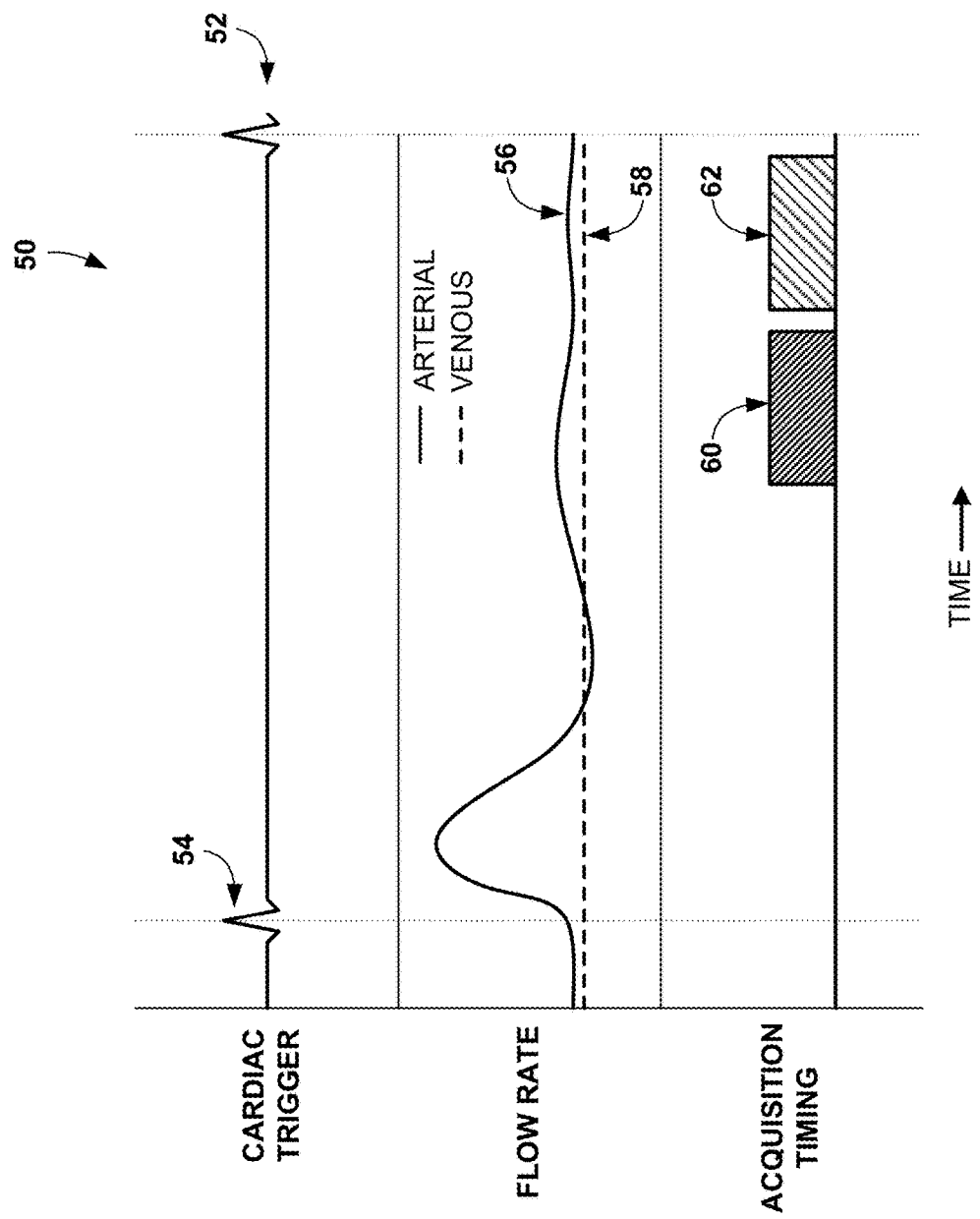
FIG. 2 is a conceptual graph illustrating example timing of single shot acquisitions of arterial and venous MR signals with respect to blood flow.

FIG. 2 is a conceptual graph 50 illustrating example timing of single shot acquisitions of arterial and venous MR signals with respect to blood flow in a MRAV technique. As shown in FIG. 2, MRI system 10 may acquire ECG signal 52 and detect R-wave 54 from signal 52. R-wave 54 may be indicative of the depolarization of the ventricles of the heart. R-wave 54 may be referred to as a start of a cardiac cycle (e.g., the cardiac trigger) due to the relatively easy detectable amplitude of the R-wave and the subsequent increase in arterial pressure that follows ventricular depolarization. Although the detection of R-waves will be described herein for the purposes of identifying the beginning of cardiac cycles, other cardiac events, such as P-waves or T-waves could be used to identify (i.e., gate) one or phases of a cardiac cycle in other examples. In other examples, detected pressure waves, accelerations of vessel walls, or heart sounds may be used to identify ventricular depolarization or other phases of a cardiac cycle. Alternatively, other techniques may be used to detect cardiac cycles and gate the timing of RF pulses and other imaging related events. For example, peripheral gating using pulse oximetry measurements may be used to detect each cardiac cycle. In another example, self-gating using real-time acquired images of the vasculature may be used to detect changing vessel diameter and each cardiac cycle.

Arterial flow signal 56 represents typical arterial flow rates during an R-R interval (i.e., a cardiac cycle). Venous flow signal 58 represents typical venous flow rates during the R-R interval. Following R-wave 54, the arterial vasculature is typically subjected to a pulse, or increased amplitude, of blood pressure and blood flow. In other words, the flow of arterial blood rapidly increases and then rapidly decreases during systole. During this increased flow rate following R-wave 54, the acquisition of arterial MR signals may be subject to flow related artifacts. In contrast to the arterial flow rates that change during the R-R interval, venous flow signal 58 indicates that venous flow remains substantially unchanged throughout the cardiac cycle. Near the end of the R-R interval (e.g., during the second half of the cardiac cycle), the flow rates in the arteries and similar sized veins may be substantially similar. Since the flow rate of blood in veins does not substantially change during the R-R interval, the acquisition of venous MR signals may not be limited to a particular temporal location within the R-R interval.

Example arterial acquisition block 60 and venous acquisition block 62 are provided with respect to the R-R interval started with R-wave 54. Arterial acquisition block 60 may represent RF excitation pulses and the corresponding detected arterial MR signals and suppressed venous MR signals. Venous acquisition block 62 may represent RF excitation pulses and the corresponding detected venous MR signals and suppressed arterial MR signals. As will be described in detail below, arterial acquisition block 60 and venous acquisition block 62 may represent respective single shot acquisitions of desired arterial and venous MR signals.

Since the flow rates of arterial flow signal 56 become substantially steady near the end of the R-R interval, the pulse sequence of MRAV may include arterial acquisition block 60 and venous acquisition block 62 positioned near the end of the R-R interval. Alternatively, venous acquisition block 62 may be located earlier in the R-R interval (e.g., during a period of rapid arterial flow) without motion artifacts because the venous flow rate is substantially constant during the entire R-R interval. Additional RF saturation pulses (e.g., preparatory pulses) selected to suppress arterial or venous blood inflow may also be provided prior to arterial acquisition block 60 and venous acquisition block 62. However, the acquisition of venous signals early in the cardiac cycle (e.g., during pulsatile arterial flow and higher arterial flow rates) may complicate the suppression of MR signals from arterial blood. It may be difficult to accurately time the arterial preparatory pulses at the higher flow rates such that arterial blood with suppressed MR signals is present within the venous imaging slice. The exact timing scheme for each of arterial acquisition block 60 and venous acquisition block 62 may vary along with the order of preparatory pulses in other examples, such as those presented in FIGS. 3A-3E.

FIGS. 3A-3E are conceptual timing diagrams of example radio frequency (RF) pulse schemes for MRAV. In each of FIGS. 3A-3E, RF pulses of each given pulse sequence may be grouped and represented by separate blocks for simplicity of explaining variations in pulse schemes (e.g., different pulse sequences). Each block may include one or more RF pulses, such as RF saturation pulses and/or RF excitation pulses. The dimensions (e.g., width and height) and shading of each block do not necessarily represent different durations of RF pulses or different parameters of the RF pulses in each block.

In some examples, pulse sequence server 20, one or more processors, and/or a computing device may be configured to perform the processes of MRAV. As generally described herein, the MRAV technique may include acquiring a signal indicative of a start of a cardiac cycle of a subject. For example, the signal may be an ECG signal where each detected R-wave indicates the start of each respective cardiac cycle. In addition, MRAV technique may include performing, by one or more processors, a pulse sequence that directs a MRI system to perform various functions.

For example, the pulse sequence may direct the MRI system to apply one or more RF saturation pulses to one or more slabs (e.g., spatial saturation bands) such that MR signals indicative of blood that flows into one or more imaging slices are substantially suppressed. In this manner, RF saturation pulses may be applied to a single slab to suppress MR signals in one or more imaging slices. Alternatively, the RF saturation pulses may be applied to two slabs to suppress MR signals in respective imaging slices.

In addition, the pulse sequence may direct the MRI system to acquire arterial specific k-space data from the subject following the application of one or more RF excitation pulses. The arterial k-space data may be indicative of arterial MR signals and substantially suppressed venous MR signals. The pulse sequence may also direct the MRI system to acquire venous specific k-space data from the subject following the application of one or more RF excitation pulses. The venous k-space data may be indicative of venous MR signals and substantially suppressed arterial MR signals. Both of the arterial k-space data and the venous k-space data may each be indicative of respective MR signals detected during a single cardiac cycle. The process may also include reconstructing, from the acquired arterial k-space data, an image that represents arterial vasculature of the subject and reconstructing, from the acquired venous k-space data, an image that represents venous vasculature of the subject.

In this manner, the MRI system may be configured to, within a single cardiac cycle, acquire k-space data with detected arterial blood in the arterial vasculature and substantially undetected venous blood and k-space data with detected venous blood in the venous vasculature and substantially undetected arterial blood. In some examples, each of the k-space data may be acquired as a single shot in coordination with the application of the respective one or more RF excitation pulses. The single shot acquisitions may be two-dimensional. Alternatively, the single shot acquisitions may be one-dimensional or even three-dimensional.

The timing of any RF saturation pulses and the RF excitation pulses may be selected to minimize unwanted artifacts within the obtained MR signals of each imaging slice. For example, the MRAV process may include performing the pulse sequence that directs the MRI system to abstain (e.g., wait) from application of any RF pulses during a period of time between the application of the one or more RF saturation pulses and the application of one or more RF excitation pulses for acquisition of MR signals. This period of time may be referred to as the preparation time ("PT") and may allow for high flow rates of arterial blood to dissipate before acquiring MR signals. Arterial specific imaging slices may be not obtained during the PT, but venous specific imaging slices may be obtained during the PT since venous blood maintains relatively constant low flow rates. In other words, the period of time of the PT may be selected such that the application of one or more RF excitation pulses for arterial MR signals occurs during diastolic inflow of arterial blood into a the imaging slice of the arterial specific k-space data.

When the MRI system is directed to apply RF saturation pulses to substantially suppress MR signals of venous or arterial blood, the suppression of arterial MR signals and venous MR signals may be performed by applying RF saturation pulses to different spatial regions of the subject. For example, the pulse sequence may direct the MRI system to apply an arterial specific RF saturation pulse to a slab (e.g., a band or region) such that MR signals indicative of venous blood that flows into the arterial specific imaging slice of the arterial k-space data are substantially suppressed. In addition, the pulse sequence may direct the MRI system to apply a venous specific RF saturation pulse to a different slab such that MR signals indicative of arterial blood that flows into the venous specific imaging slice of the venous k-space data are substantially suppressed. In other words, RF saturation pulses may be applied to a region of the patient from which blood will flow into the later acquired imaging slice. RF saturation pulses to suppress unwanted MR signals may thus be applied upstream from the intended imaging slice of the vessel location within which blood is not to be imaged. The RF saturation pulses may suppress blood in a slab such that when MR signals of the imaging slice are obtained, the suppressed blood would have flowed into the imaging slice. For this reason, the spatial width of the slab and timing of the RF saturation pulses may need to be determined in order to effectively suppress unwanted signals from a desired imaging slice.

The different pulse schemes illustrated by FIGS. 3A-3E represent different orders of RF saturation pulses (e.g., preparatory blocks) and RF excitation pulses (e.g., acquisition blocks) to achieve MRAV. Preparatory blocks may be representative of one or more RF saturation pulses applied to one or more slabs such that MR signals indicative of blood that flows into one or more imaging slices are substantially suppressed. For example, arterial preparatory blocks may indicate venous blood MR signals are suppressed and venous preparatory blocks may indicate arterial blood MR signals are suppressed. Acquisition blocks may be representative of RF excitation pulses applied to the subject to acquire k-space data indicative of desired blood with non-suppressed MR signals and substantially suppressed MR signals of blood subjected to the RF saturation pulses of the corresponding preparatory block. For example, arterial acquisition blocks may indicate non-suppressed arterial blood MR signals are obtained and venous acquisition blocks may indicate non-suppressed venous blood MR signals are obtained. Although the process will be described with respect to pulse sequence server 20 of FIG. 1, other processors or systems may perform the process.

In the example of FIG. 3A, detected R-waves 66A and 66B indicate the start of consecutive cardiac cycles. Pulse sequence server 20 may first wait a time period A1 from the detected R-wave 66A to the desired application of arterial preparatory block 68 (e.g., an RF saturation pulse for suppressing venous blood and background tissue MR signals). After time period A2 elapses, pulse sequence server 20 may control MRI system 10 to apply the pulses of venous preparatory block 70. After waiting the duration of time period A3, pulse sequence server 20 may then control MRI system 10 to apply the pulses of arterial acquisition block 72. Pulse sequence server 20 may subsequently control MRI system 10 to apply the pulses of venous acquisition block 74 after waiting the time period of A4. The pulses of all blocks 68, 70, 72, and 74 may occur within the R-R interval between R-waves 66A and 66B.

The durations of each time periods A1, A2, A3, and A4 may be modified to achieve the desired suppression of unwanted MR signals and acquisitions of desired MR signals during desired blood flow rates. Although the period A2+A3 may be substantially equal to the period A3+A4, these periods can be different in some examples. In some examples, A1 may generally between approximately 10 ms and 300 ms, A2 may generally be between approximately 10 ms and 300 ms, A3 may be between approximately 10 ms and 300 ms, and A4 may be between approximately 100 ms and 500 ms. However, each period of time may be greater than or less than these example durations.

The example of FIG. 3B is similar to the example of FIG. 3A. However, the arterial preparatory block and venous preparatory block have switched order within the pulse scheme. By applying the venous preparatory block before the arterial preparatory block, a greater period of time (e.g., B2+B3+B4) may be provided to allow a greater preparation time for the venous acquisition block. Therefore, in the example of FIG. 3A, detected R-waves 76A and 76B indicate the start of consecutive cardiac cycles. Pulse sequence server 20 may first wait a time period B1 from the detected R-wave 76A to the desired application of arterial preparatory block 78 (e.g., an RF saturation pulse for suppressing arterial blood and background tissue MR signals). After time period B2 elapses, pulse sequence server 20 may control MRI system 10 to apply the pulses of arterial preparatory block 80. After waiting the duration of time period B3, pulse sequence server 20 may then control MRI system 10 to apply the pulses of arterial acquisition block 82. Pulse sequence server 20 may subsequently control MRI system 10 to apply the pulses of venous acquisition block 84 after waiting the time period of B4. The pulses of all blocks 78, 80, 82, and 84 may occur within the R-R interval between R-waves 76A and 76B.

The durations of each time periods B1, B2, B3, and B4 may be modified to achieve the desired suppression of unwanted MR signals and acquisitions of desired MR signals during desired blood flow rates. In some examples, B1 may generally between approximately 10 ms and 300 ms, B2 may generally be between approximately 10 ms and 300 ms, B3 may be between approximately 10 ms and 300 ms, and B4 may be between approximately 100 ms and 500 ms. However, each period of time may be greater than or less than these example durations.

In the example of FIG. 3C, both preparatory blocks occur prior to any acquisition blocks. Detected R-waves 86A and 86B indicate the start of consecutive cardiac cycles. Pulse sequence server 20 may first wait a time period C1 from the detected R-wave 86A to the desired application of venous preparatory block 88. After time period C2 elapses, pulse sequence server 20 may control MRI system 10 to apply the pulses of arterial preparatory block 90. After waiting the duration of time period C3, pulse sequence server 20 may then control MRI system 10 to apply the pulses of venous acquisition block 92. Pulse sequence server 20 may subsequently control MRI system 10 to apply the pulses of arterial acquisition block 94 after waiting the time period of C4. The pulses of all blocks 88, 90, 92, and 94 may occur within the R-R interval between R-waves 86A and 86B.

The durations of each time periods C1, C2, C3, and C4 may be modified to achieve the desired suppression of unwanted MR signals and acquisitions of desired MR signals during desired blood flow rates. In some examples, C1 may generally between approximately 10 ms and 300 ms, C2 may generally be between approximately 10 ms and 300 ms, C3 may be between approximately 10 ms and 300 ms, and C4 may be between approximately 100 ms and 500 ms. However, each period of time may be greater than or less than these example durations.

In the example of FIG. 3D, both preparatory blocks occur prior to any acquisition blocks, and venous preparatory block 98 occurs within the prior cardiac cycle. Detected R-waves 96A and 96B indicate the start of consecutive cardiac cycles. Pulse sequence server 20 may determine when to control MRI system 10 to apply the venous preparatory pulses based on an anticipated occurrence of R-wave 96A. From this anticipated R-wave 96A, pulse sequence server 20 may control MRI system 10 to apply the venous preparatory block 98 a time period D1 prior to the anticipated R-wave 96A. Venous preparatory block 98 may be prior to R-wave 96A to ensure that the venous blood flow will reach the imaging slice for venous acquisition block 102. After time period D2 elapses from the detected R-wave 96A, pulse sequence server 20 may control MRI system 10 to apply the pulses of arterial preparatory block 100. After waiting the duration of time period D3, pulse sequence server 20 may then control MRI system 10 to apply the pulses of venous acquisition block 102. Pulse sequence server 20 may subsequently control MRI system 10 to apply the pulses of arterial acquisition block 104 after waiting the time period of D4.

The durations of each time periods D1, D2, D3, and D4 may be modified to achieve the desired suppression of unwanted MR signals and acquisitions of desired MR signals during desired blood flow rates. In some examples, D1 may generally between approximately 10 ms and 300 ms, D2 may generally be between approximately 10 ms and 300 ms, D3 may be between approximately 10 ms and 300 ms, and D4 may be between approximately 100 ms and 500 ms. However, each period of time may be greater than or less than these example durations.

In the example of FIG. 3E, detected R-waves 105A and 105B indicate the start of consecutive cardiac cycles. Pulse sequence server 20 may first wait a time period E1 from the detected R-wave 105A to the desired application of venous preparatory block 106. After time period E2 elapses, pulse sequence server 20 may control MRI system 10 to apply the pulses of venous acquisition block 107. After waiting the duration of time period E3, pulse sequence server 20 may then control MRI system 10 to apply the pulses of arterial preparatory block 108. Pulse sequence server 20 may subsequently control MRI system 10 to apply the pulses of arterial acquisition block 109 after waiting the time period of E4. The pulses of all blocks 106, 107, 108, and 109 may occur within the R-R interval between R-waves 105A and 105B.

The durations of each time periods E1, E2, E3, and E4 may be modified to achieve the desired suppression of unwanted MR signals and acquisitions of desired MR signals during desired blood flow rates. In some examples, E1 may generally between approximately 10 ms and 300 ms, E2 may generally be between approximately 10 ms and 300 ms, E3 may be between approximately 100 ms and 500 ms, and E4 may be between approximately 10 ms and 300 ms. However, each period of time may be greater than or less than these example durations.

In the examples of FIGS. 3A-3E, each of the preparatory blocks (e.g., the RF saturation pulses that suppress venous and arterial blood MR signals), occur in a different time and in a different spatial slab of the subject. However, in some examples, the same one or more RF saturation pulses may be applied to a single slab of the subject. In this manner, the slab may be spatially positioned and the RF saturation pulses may be timed such that the suppressed MR signals of both arterial blood and venous blood within the single slab reaches their respective imaging slice when the MR signals are obtained for each slice. FIGS. 5E and 5F illustrate an example of this single slab. In this manner, pulse sequence server 20 may be configured to control MRI system 10 to apply one or more RF saturation pulses to one slab such that MR signals indicative of venous blood that flows into an arterial imaging slice of the arterial k-space data are substantially suppressed and MR signals indicative of arterial blood that flows into a venous imaging slice of the venous k-space data are substantially suppressed. The imaging slices may be located outside of the slab or within the slab.

In some examples, the pulse schemes described herein may include RF saturation pulses within the acquisition blocks. For example, one or more RF saturation pulses may be applied in a selective or non-selective manner to an imaging slice prior to one or more RF excitation pulses. These RF saturation pulses proximate in time to the RF excitation pulses may substantially suppress background artifacts, fat, flow artifacts, or any other unwanted MR signals from the imaging slice.

Preparatory pulses (e.g., RF saturation pulses to suppress fat, background artifacts, and/or directionally opposed venous and arterial signals) may be applied during any or all open intervals prior to obtaining the desired MR signals. The effectiveness of preparatory pulses to suppress undesired MR signals may be optimized by adjusting the spatial location and temporal location of the pulses and flip angles of the pulses. Although single shot acquisition is generally described herein for the pulse sequence of distinct arterial and venous acquisition blocks, continuous and/or multiplexed variants are also contemplated. For example, arterial and venous signals may be retrospectively segmented from a continuous acquisition of a single slice. In another example, arterial and venous signals at separate slice locations may be acquired simultaneously using slice multiplexing techniques.

Figure 4:
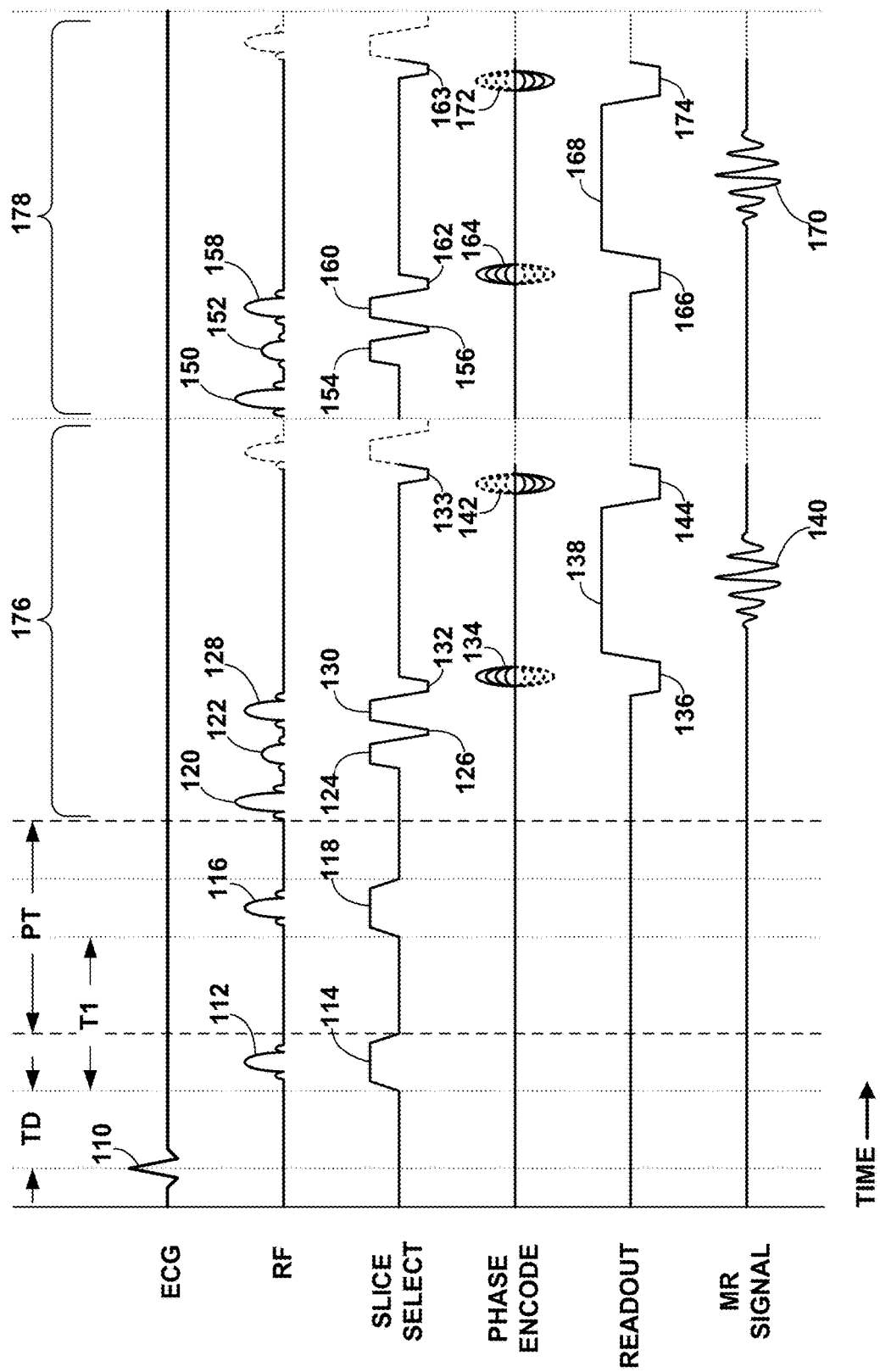
FIG. 4 is a conceptual drawing illustrating an example pulse sequence performed by the MRI system of FIG. 1.

FIG. 4 is a conceptual drawing illustrating an example pulse sequence performed by MRI system 10 of FIG. 1. The pulse sequence of FIG. 4 may generally correspond to the pulse scheme described above with respect to FIG. 3A. The pulse sequence of FIG. 4 may be similarly adapted according to the timing of pulse schemes in FIGS. 3B-3D and/or other pulse sequences.

The pulse sequence of FIG. 4 is cardiac gated, such that the acquisition of k-space data in the arterial imaging slice and the venous imaging slice is timed with respect to the flow of arterial blood. Specifically, the pulse sequence may be timed to be played out with respect to the peak of the R-wave 110 in a concurrently acquired ECG. It should be appreciated by those skilled in the art, however, that other methods for cardiac synchronization of the following pulse than relying on an ECG signal are possible. For example, cardiac synchronization can be achieved using self-gating techniques that rely on measurement of flow signal or phase.

Turning now to the pulse sequence, a slab-selective RF saturation pulse 112 is first provided in the presence of a slab-selective gradient 114. RF saturation pulse 112 may correspond to arterial preparatory block 68 of FIG. 3A. The application of this slab-selective RF saturation pulse 112 may have the effect of suppressing the signals from background tissues as well as those venous spins that are present in the prescribed slice, and those venous spins that will flow into the imaging slice at some future time. The flip angle for this slab-selective RF saturation pulse 112 is typically about 90 degrees; however, larger or smaller flip angles may be desirable in some circumstances. Slab-selective RF saturation pulse 112 may be timed to occur at a preset time delay ("TD") after the occurrence of the R-wave 110. For example, TD may be set in the range of 0 to 100 milliseconds (ms). In other examples, TD may be set to smaller or larger durations of time depending upon the duration of the single shot acquisition times and desired non-RF durations.

The duration of time that is allowed to pass after the application of the slab-selective RF saturation pulse 112 may be referred to as the "preparation time" ("PT"). The preparation time may be the period of time between the application of the slice or slab-selective RF saturation pulse 113 and the zero line of k-space. This duration of time is specifically tailored to coincide with the rapid inflow of arterial blood into a prescribed imaging slice, and so that the zero line of k-space is acquired during the slow, diastolic inflow of arterial blood into the arterial imaging slice. More particularly, a central portion of k-space may be sampled during the slow, diastolic inflow of arterial blood into the arterial imaging slice before the peripheral regions of k-space are sampled. The result of this is a substantial suppression of flow-based image artifacts in the arterial imaging slice. Put another way, this provides a method that may be substantially insensitive to flow velocities in the prescribed image slice. Moreover, the PT may allow for a maximal inflow of unsaturated arterial spins into the imaging slice, such that an improved discrimination of arterial spins is provided in the resultant images. This is even so when the patient's vasculature is significantly impacted by vascular diseases such as peripheral vascular disease ("PVD"). Exemplary values of PT in this configuration of the pulse sequence are on the order of 300 ms. However, the values of PT may be between approximately 50 ms and 400 ms. In other examples, the values of PT may be lower than 50 ms or greater than 400 ms.

During the PT, a slab-selective RF saturation pulse 116 is first played out in the presence of a slab-selective gradient 118. RF saturation pulse 116 may correspond to venous preparatory block 70 of FIG. 3A. The application of this slab-selective RF saturation pulse 116 may have the effect of suppressing the signals from background tissues as well as those arterial spins that are present in the prescribed slice, and those arterial spins that will flow into the imaging slice at some future time. The flip angle for this slab-selective RF saturation pulse 116 is typically about 90 degrees; however, larger or smaller flip angles may be desirable in some circumstances. Slab-selective RF saturation pulse 116 may be timed to occur at a preset time delay after the occurrence of the R-wave 110 or after the timed application of RF saturation pulse 112. Although RF saturation pulses 112 and 116 (and slab-selective gradient 114 and 118) may be defined by substantially the same parameters, the RF saturation pulses 112 and 116 may be defined by one or more different parameters in other examples.

After the PT has passed, the pulse sequence proceeds with data acquisition for the arterial imaging slice (with venous MR signals being suppressed), which is accomplished, for example, with a single shot balanced steady-state free procession (SSFP) gradient echo pulse sequence. First, a spectrally selective fat saturation RF pulse 120 is applied to further suppress unwanted MR signals originating from fat tissue. This is subsequently followed by a slice-selective period of RF catalyzation (such as an a/2 magnetization RF pulse) 122 that is played out in the presence of a slice-selective gradient 124, where a is a user selected flip angle. The slice-selective gradient includes a rephasing lobe 126 that acts to mitigate unwanted phase accruals that occur during the application of the slice-selective gradient 124. This portion of the pulse sequence may include a slice-selective RF excitation pulse 128 that is played out in the presence of a slice-selective gradient pulse 130 to produce transverse magnetization in a prescribed slice. The slice-selective gradient includes a rephasing lobe 132 that acts to mitigate unwanted phase accruals that occur during the application of the slice-selective gradient 130. After excitation of the spins in the slice, a phase encoding gradient pulse 134 is applied to position encode the MR signal 140 along one direction in the slice. A readout gradient pulse 138 is also applied after a dephasing gradient lobe 136 to position encode the MR signal 140 along a second, orthogonal direction in the slice. MR signal 140 may be indicative of an arterial imaging slice with suppressed venous MR signals.

Like the slice-selective gradient 130, the readout gradient 138 also includes a rephasing lobe 144 that acts to mitigate unwanted phase accruals.

To maintain the steady state condition, the integrals along the three gradients each sum to zero during the repetition time period. To accomplish this, a rewinder gradient lobe 142 that is equal in amplitude, but opposite in polarity of the phase encoding gradient 134, is played out along the phase encoding gradient axis. Likewise, a dephasing lobe 133 is added to the slice select gradient axis, such that the dephasing lobe 133 precedes the repetition of the slice-selective gradient 130 in the next TR period. As is well known in the art, the reading out of MR signals following the single shot of the RF excitation pulse 128 is repeated and the amplitude of the phase encoding gradient 134 and its equal, but opposite rewinder 142 are stepped through a set of values to sample 2D k-space in a prescribed manner. It should be appreciated by those skilled in the art that any number of data acquisition schemes can be employed to acquire k-space data instead of balanced SSFP. For example, spoiled gradient echo, spiral acquisition, or echo planar imaging ("EPI") pulse sequences can alternatively be utilized.

The pulses and signals within bracket 176, including the repeated TR period, may correspond to the arterial acquisition block 72 of FIG. 3A. The pulses and signals within bracket 178 may correspond to the venous acquisition block 74 of FIG. 3B. In some examples, the RF pulses and gradients applied to the subject during bracket 176 to obtain the arterial imaging slice may be the same RF pulses and gradients applied to the subject to obtain the venous imaging slice. In other examples, obtaining arterial and venous imaging slices may require one or more different pulses and/or gradients. Generally, the pulses applied during bracket 176 may not overlap in time with the pulses applied during bracket 178. However, in other examples, some pulses within bracket 176 may overlap in time with the pulses in bracket 178 when the pulses are multiplexed in order to acquire multiple slices simultaneously. In alternative examples, at least some pulses within bracket 176 may overlap in time with at least some pulses in bracket 178 when acquisition is a continuous concatenated acquisition of arterial and venous k-space data. In this manner, the RF excitation pulses (and/or corresponding RF saturation pulses during the preparatory period) may be multiplexed or interleaved between imaging slices at respectively different locations. In addition, the readout of respective signals, and/or the transmission or reception of any other signals, may be multiplexed at their respective locations.

The pulses and gradients of bracket 178 may also begin after a time period from the delivery of RF saturation pulse 112 or RF saturation pulse 116. Alternatively, the pulses and gradients of bracket 178 may begin after a time period from R-wave 110. A spectrally selective fat saturation RF pulse 150 may be applied to further suppress unwanted MR signals originating from fat tissue. This is subsequently followed by a slice-selective period of RF catalyzation (such a an a/2 magnetization RF pulse) 152 that is played out in the presence of a slice-selective gradient 154, where a is a user selected flip angle. The slice-selective gradient includes a rephasing lobe 156 that acts to mitigate unwanted phase accruals that occur during the application of the slice-selective gradient 154. This portion of the pulse sequence may include a slice-selective RF excitation pulse 158 that is played out in the presence of a slice-selective gradient pulse 160 to produce transverse magnetization in a prescribed slice. The slice-selective gradient includes a rephasing lobe 162 that acts to mitigate unwanted phase accruals that occur during the application of the slice-selective gradient 160. After excitation of the spins in the slice, a phase encoding gradient pulse 164 is applied to position encode the MR signal 170 along one direction in the slice. A readout gradient pulse 168 is also applied after a dephasing gradient lobe 166 to position encode the MR signal 170 along a second, orthogonal direction in the slice. MR signal 170 may be indicative of a venous imaging slice with suppressed arterial MR signals. Like the slice-selective gradient 160, the readout gradient 168 also includes a rephasing lobe 174 that acts to mitigate unwanted phase accruals.

To maintain the steady state condition, the integrals along the three gradients each sum to zero during the repetition time period. To accomplish this, a rewinder gradient lobe 172 that is equal in amplitude, but opposite in polarity of the phase encoding gradient 164, is played out along the phase encoding gradient axis. Likewise, a dephasing lobe 163 is added to the slice select gradient axis, such that the dephasing lobe 163 precedes the repetition of the slice-selective gradient 160 in the next TR period. As was described above, it is well known in the art that the reading out of MR signals following the single shot of the RF excitation pulse 158 is repeated and the amplitude of the phase encoding gradient 164 and its equal, but opposite rewinder 172 are stepped through a set of values to sample 2D k-space in a prescribed manner. It should be appreciated by those skilled in the art that any number of data acquisition schemes can be employed to acquire k-space data instead of balanced SSFP. For example, spoiled gradient echo, spiral acquisition, or echo planar imaging ("EPI") pulse sequences can alternatively be utilized.

Each of the RF pulses, and corresponding gradients, are representative of pulses and gradients that may be used within the pulse sequence. In some examples, one RF pulse shown in FIG. 4 may correspond to a single RF pulse. In other examples, one RF pulse may merely represent two or more RF pulses that together produce the feature described with respect to the single illustrated pulse. In this manner, the pulse sequence of FIG. 4 is representative of the relative timing between certain types of pulses used to acquire k-space data from desired imaging slices and indicative of certain MR signals within each slice.

Although the pulse sequence of FIG. 4 was described with respect to the pulse schemes presented in FIG. 3A, similar pulse sequences may be used in conjunction with the different pulse schemes of FIGS. 3B-3D or any other pulse timing to acquire k-space data of arterial specific and venous specific imaging slices.

The MRAV techniques described herein may be enhanced through the use of additional imaging techniques. Non-Cartesian approaches may enable additional functionality. A highly efficient spiral readout trajectory, for example, could allow for relatively short acquisition windows. Data acquired from a continuous radial acquisition, for example, could be retrospectively segmented into arterial and venous datasets, and/or used to optimize the sequence preparation timing in real-time. Slice multiplexing techniques may enable shorter overall scan times by allowing simultaneous transmission and/or reception of multiple saturation bands and slices.

Although the acquisition of k-space data is generally described herein as the type of data indicative of MR signals obtained from a subject, different types of data or data structures may be used in other examples. For example, o-space data may be acquired instead of k-space data. In other words, the techniques herein contemplate the acquisition and/or use of any types of data, not just k-space data, that may be indicative of the MR signals obtained from a subject.

FIGS. 5A-5F are conceptual drawings illustrating example spatial relationships between arterial and venous imaging slices and respective saturation bands. As described herein, RF saturation pulses may be applied to one or more slabs, or bands, to substantially suppress MR signals from blood that flows into a subsequent, in time, imaging slice. Since the saturation bands produced by the RF saturation signals are targeted at moving blood, the saturation bands may be placed at spatially different locations of the MRI system and the subject. The spatial location of the saturation bands with respect to each other and with respect to the imaging slices may vary based on the available timing within the cardiac cycle and the spatial location of each imaging slice. Other spatial and timing configurations are also possible.

For each of FIGS. 5A-5F, artery 180 is shown to carry blood in a direction opposite that of vein 182. Although artery-vein pairs may not be substantially parallel in a subject, these parallel vessels are provided for illustration and the techniques described herein may be equally applicable to non-parallel arteries and veins. Each saturation band is also shown orthogonal to and across both of artery 180 and 182. Although the saturation band may only need to be applied to the artery or vein that carries the blood targeted for suppression of MR signals, limiting the saturation band to only one of the vessels may be impractical or impossible in practice. Each saturation band may be generated by RF saturation pulses defined by the same parameter values, but different parameter values may be used to generate RF saturation pulses of different saturation bands in other examples.

Figure 5A:
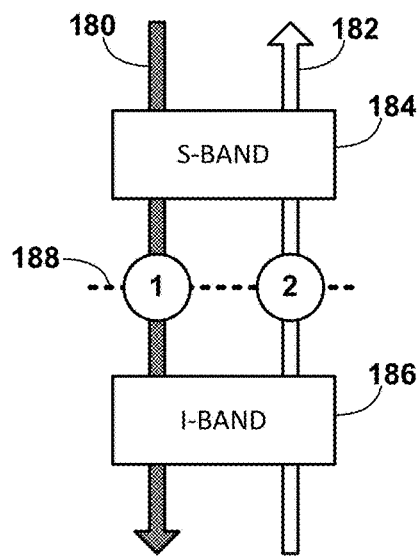
FIGS. 5A-5F are conceptual drawings illustrating example spatial relationships between arterial and venous imaging slices and respective saturation bands.

FIG. 5A illustrates an example configuration of saturation bands when a single location has been selected for both arterial and venous imaging slices. Saturation band 186 is applied inferior to imaging slice 188 such that venous flow through saturation band 186 includes suppressed MR signals when the arterial imaging slice (1) is obtained. Saturation band 184 is applied superior to imaging slice 188 such that arterial flow through saturation band 184 includes suppressed MR signals when the venous imaging slice (2) is obtained. Therefore, the arterial and venous imaging slices may be obtained (e.g., the respective single shot acquisitions are performed) at different times. The timing and/or width of each of saturation bands 184 and 186 may be selected based on expected blood flows when the imaging slices are obtained during the same cardiac cycle. Since a single slice location (e.g., the location of imaging slice 188) may be used to acquire atrial and venous imaging slices, retrospective segmentation of arterial and venous signals may be used to reconstruct the respective arterial and venous images from the continuous or semi-continuous acquisition of MR signals at the same location.

Figure 5B:
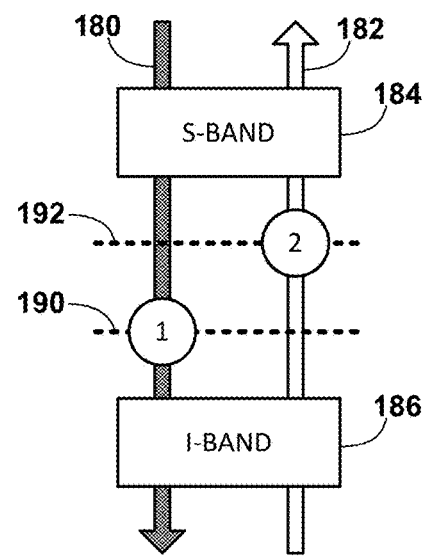

FIG. 5B illustrates an example configuration of saturation bands when each of the arterial and venous imaging slices occur at different spatial locations between the saturation bands. Arterial and venous imaging slices may be spatially separated from each other when acquired within the same heartbeat to minimize interactions (e.g., saturation, recovery, and/or steady-state effects) between MR signals in subsequently acquired slices. Saturation band 186 is applied inferior to arterial imaging slice 190 such that venous flow through saturation band 186 includes suppressed MR signals when the arterial imaging slice 190 is obtained. Saturation band 184 is applied superior to imaging slice 192 such that arterial flow through saturation band 184 includes suppressed MR signals when venous imaging slice 192 is obtained. Therefore, the saturation bands and arterial and venous imaging slices may be obtained (e.g., the respective single shot acquisitions are performed) at different times. The timing and/or width of each of saturation bands 184 and 186 may be selected based on expected blood flows when the imaging slices are obtained during the same cardiac cycle.

Figure 5C:
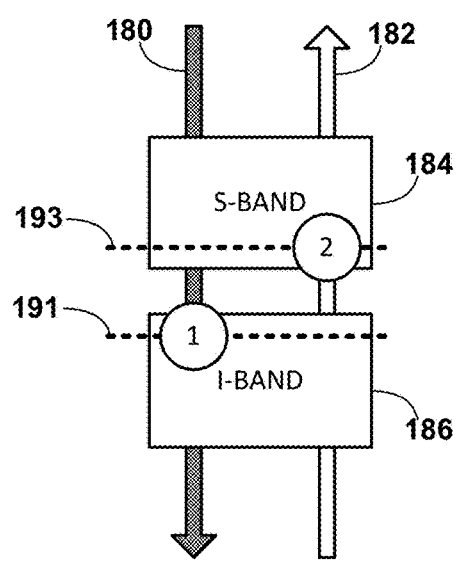

FIG. 5C illustrates an example configuration of saturation bands when each of the arterial and venous imaging slices occur at different spatial locations and at locations within the respective saturation bands. FIG. 5C may be similar to the configuration of FIG. 5B, except that imaging slices 191 and 193 are now located within the respective saturation bands 184 and 186 to suppress background MR signals in addition to MR signals from flowing blood. In the example of FIG. 5C, saturation band 186 is applied inferior to, and including, arterial imaging slice 191 such that venous flow through saturation band 186 includes suppressed MR signals when arterial imaging slice 191 is obtained. Saturation band 184 is applied superior to, and including, imaging slice 193 such that arterial flow through saturation band 184 includes suppressed MR signals when venous imaging slice 193 is obtained. Therefore, the saturation bands and arterial and venous imaging slices may be obtained (e.g., the respective single shot acquisitions are performed) at different times. The timing and/or width of each of saturation bands 184 and 186 may be selected based on expected blood flows when the imaging slices are obtained during the same cardiac cycle and to include the respective imaging slices.

Figure 5D:
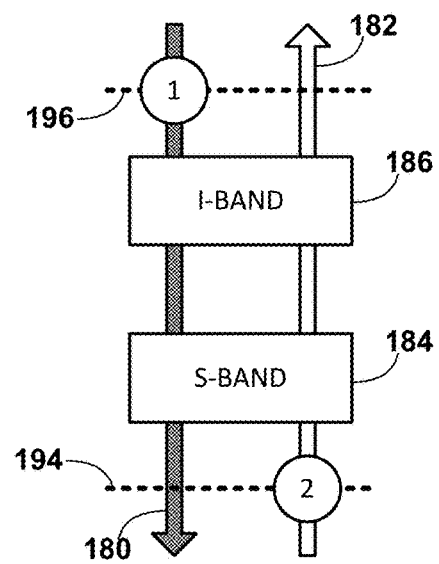
Figure 5E:
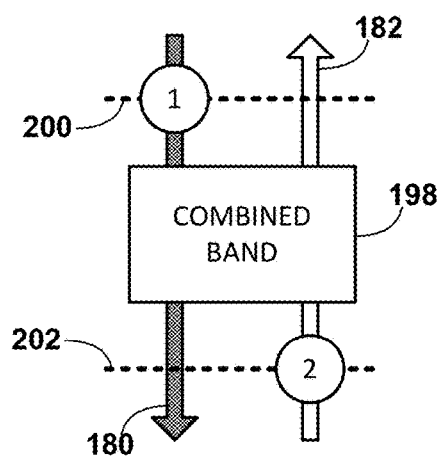
Figure 5F:
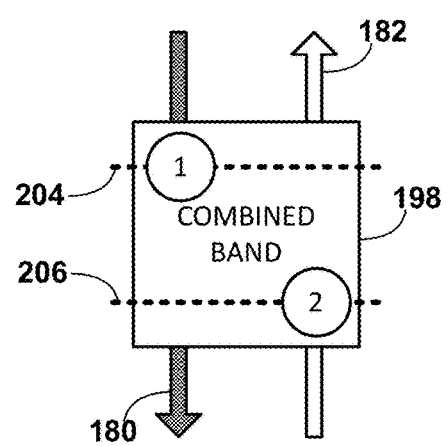

FIG. 5D illustrates an example configuration of saturation bands when each of the arterial and venous imaging slices occur at different spatial locations outside of the saturation bands. Saturation band 186 is applied inferior to arterial imaging slice 196 such that venous flow through saturation band 186 includes suppressed MR signals when the arterial imaging slice 196 is obtained. Saturation band 184 is applied superior to venous imaging slice 194 such that arterial flow through saturation band 184 includes suppressed MR signals when venous imaging slice 194 is obtained. Therefore, the saturation bands and arterial and venous imaging slices may be obtained (e.g., the respective single shot acquisitions are performed) at different times. The timing and/or width of each of saturation bands 184 and 186 may be selected based on expected blood flows when the imaging slices are obtained during the same cardiac cycle.

FIG. 5E illustrates an example configuration of a single saturation band positioned between each of the arterial and venous imaging slices occurring at different spatial locations outside of the saturation bands. Saturation band 198 is applied inferior to arterial imaging slice 200 such that venous flow through saturation band 198 includes suppressed MR signals when the arterial imaging slice 200 is obtained. Saturation band 198 is also applied superior to venous imaging slice 202 such that arterial flow through saturation band 198 includes suppressed MR signals when venous imaging slice 202 is obtained. Therefore, the arterial and venous imaging slices may be obtained (e.g., the respective single shot acquisitions are performed) at different times, but saturation band 198 is a single saturation band with a single set of RF saturation pulses. The timing and/or width of saturation band 198 may be selected based on expected blood flows when the imaging slices are obtained during the same cardiac cycle.

FIG. 5F may be similar to that of FIG. 5E and illustrates an example configuration of arterial and venous imaging slices 204 and 206, respectively, positioned within a single saturation band 198. Saturation band 198 is applied over the same position as arterial imaging slice 204 such that venous flow through saturation band 198 includes suppressed MR signals when the arterial imaging slice 204 is obtained. Saturation band 198 is also applied over the same position as venous imaging slice 206 such that arterial flow through saturation band 198 includes suppressed MR signals when venous imaging slice 206 is obtained. Saturation band 198 may not suppress MR signals of the arterial blood in arterial imaging slice 204 or the MR signals of the venous blood in venous imaging slice 206 because saturation band 198 may be applied prior to the imaging slices 204 and 206. In other words, the blood having non-suppressed MR signals was outside of saturation band 198 when saturation band 198 was applied to the subject. The timing and/or width of saturation band 198 may be selected based on expected blood flows when the imaging slices are obtained during the same cardiac cycle.

The slabs, or saturation bands, used to suppress MR signals from blood may be relatively thick (in spatial terms) to suppress a sufficient volume of blood such that the imaging slices contain the blood with suppressed MR signals and the directionally opposed blood with unsuppressed MR signals. In other examples, thin-slab variations of both Cartesian and non-Cartesian approaches may be suited for higher-velocity vascular anatomy, such as the vasculature of the abdomen or neck.

FIGS. 5A-F generally describe artery 180 and vein 182 as approximately parallel to each other. Although the techniques herein may generally be described as relating to two or more vessels with directionally-opposed flow, the blood flow direction and corresponding vasculature orientation does not need to be exactly parallel and within a single plane. Instead, the opposing flows from each vessel may be generally opposing, e.g., blood from one vessel is flowing toward one area of the subject and blood from another vessel is flowing toward a different area of the subject. Opposing flow directions may be generally described by an angle in space between two vectors defining the flow direction. For example, flows may be considered as directionally-opposed when the angle between the vectors of flow is between approximately 90 degrees and 180 degrees, where 180 degrees would indicate flows in exactly opposite directions (as shown in FIGS. 5A-5F). In another example, flows may be considered as directionally-opposed when the angle between the vectors of flow is between approximately 135 degrees and 180 degrees. In any case, the techniques described herein may be applied to any two or more vessels in which blood with suppressed MR signals will flow into an imaging slice at another location to effectively enhance the un-suppressed MR signals of blood of a different vessel.

Figure 6:
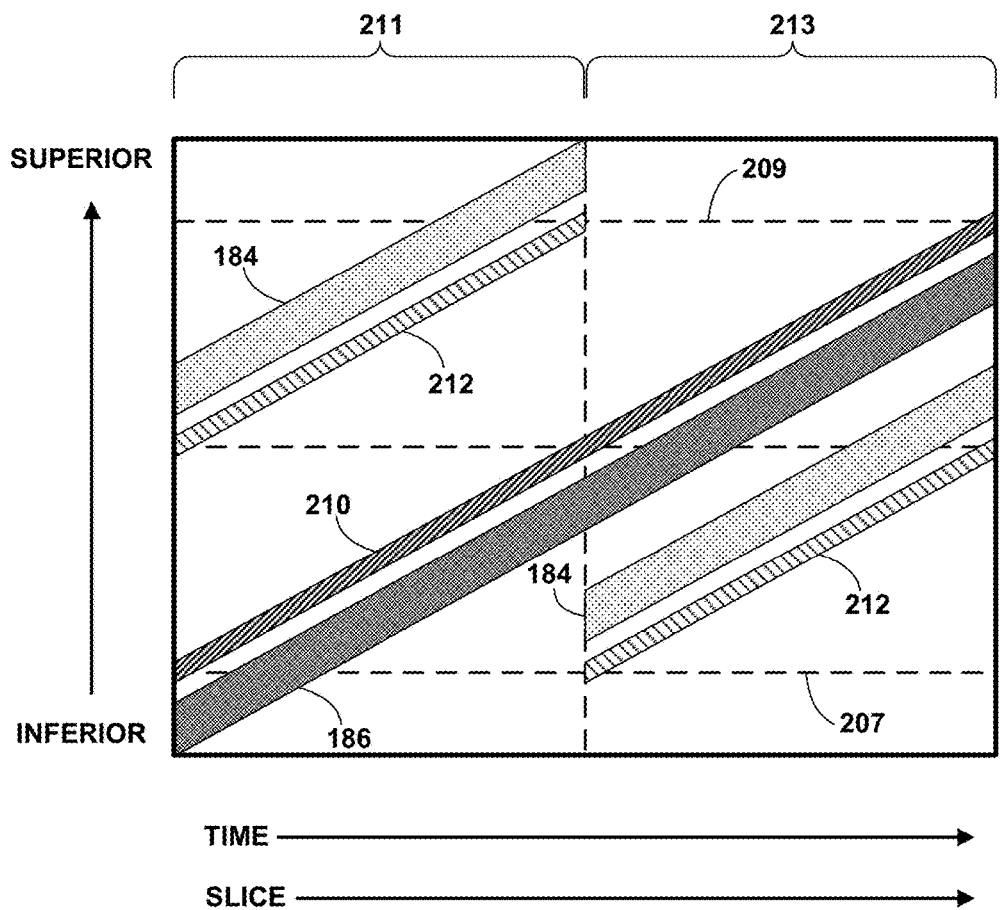
FIG. 6 is a conceptual diagram illustrating example spatial and time relationships during a scan of a subject between arterial and venous imaging slices and respective saturation bands.

FIG. 6 is a conceptual diagram illustrating example spatial and time relationships during a scan of a subject between arterial and venous imaging slices 210 and 212, respectively, and saturation bands 184 and 186. FIG. 6 may illustrate a timewise application of the spatial locations of FIGS. 5A-5F. As shown in FIG. 6, the locations of imaging slices 210 and 212 and saturation bands 184 and 86 with respect to each other may change as slices are obtained for the entire volume of the subject. As time progresses to the right, additional imaging slices are also obtained. After one set of arterial imaging slice 210 and venous imaging slice 212 are obtained during one cardiac cycle, each slice moves to a new position of the patient to image that new location. Therefore, the position of arterial imaging slices 210, venous imaging slices 212, saturation band 184, and saturation band 186 is changed by for subsequent cardiac cycles during the MRAV scan.

For example, the first portion 211 of the MRAV scan may begin with saturation bands 184 and 186 oriented to arterial imaging slice 210 and venous imaging slice 212 similar to the example of FIG. 5B. The scan may begin with arterial imaging slice 210 positioned at inferior limit 207. As new slices are obtained, all of the saturation bands 184 and 186 and imaging slices 210 and 212 move incrementally in a superior or proximal direction within the spatial domain. Once venous imaging slice 212 reaches superior limit 209 of the desired imaging space, saturation band 184 and venous imaging slice 212 may jump back to inferior limit 207. During second portion 213 of the MRAV scan, saturation bands 184 and 186 may be oriented to arterial imaging slice 210 and venous imaging slice 212 similar to the example of FIG. 5D. As new slices are obtained, all of the saturation bands 184 and 186 and imaging slices 210 and 212 again move incrementally in a superior direction until arterial imaging slice 210 reaches superior limit 209. At this point, arterial imaging slices 210 and venous imaging slices 212 have been acquired for the entire volume of the imaging space.

Although FIG. 6 illustrates saturation bands 184 and 186 and imaging slices 210 and 212 moving incrementally in a superior direction, the bands and slices may be moved incrementally in the inferior direction instead. In other examples, the movement of saturation bands 184 and 186 and imaging slices 210 and 212 may be non-incremental. Positions for new slices may jump between different locations in an organized or somewhat random order. The scheme for moving saturation bands 184 and 186 and imaging slices 210 and 212 within the MRI space may be determined at last part in consideration of residual artifacts from MR signals at adjacent tissues in space, for example. The techniques of FIG. 6 may be applied to any of the examples of FIGS. 5A-5F and other saturation band and imaging slice locations.

Figure 7:
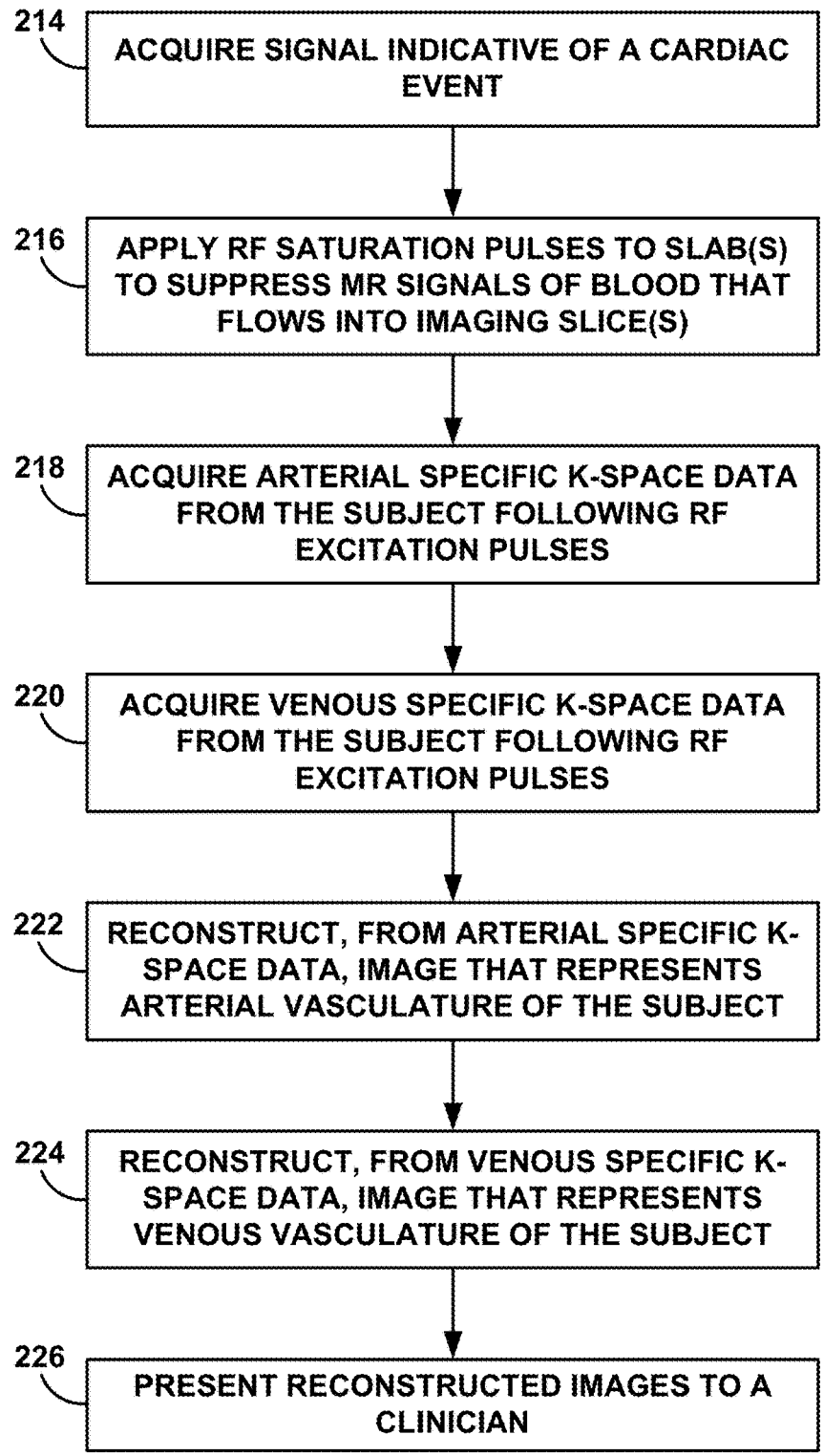
FIG. 7 is a flow diagram of an example process for employing MRAV in an MRI system.

FIG. 7 is a flow diagram of an example process for employing MRAV in an MRI system. Pulse sequence server 20 may be described as controlling MRI system to perform various functions. However, in other examples, different servers, processors, or systems may be configured to at least partially control MRI system 10 to perform the functions described herein.

Pulse sequence server 20 may be configured to control MRI system 10 to acquire a signal (e.g., an ECG signal) indicative of a cardiac event (214). The cardiac event may be a detected R-wave within the ECG signal. Pulse sequence server 20 may then perform a pulse sequence that controls MRI system 10 to perform various functions. MRI system 10 may be controlled to apply RF saturation pulses to one or more slabs, or bands, to suppress MR signals of blood that flows into one or more imaging slices (216). The RF saturation pulses may be applied to separate slabs, each slab being spatially oriented to suppress the MR signals of venous blood flowing into a respective arterial specific imaging slice and a respective venous specific imaging slice.

The pulse sequence may then control MRI system 10 to acquire arterial specific k-space data from the subject following the application of RF excitation pulses (218). The arterial specific k-space data may include non-suppressed MR signals from arterial blood and suppressed MR signals from venous blood. The pulse sequence may also control MRI system 10 to acquire venous specific k-space data from the subject following the application of RF excitation pulses (220). The venous specific k-space data may include non-suppressed MR signals from venous blood and suppressed MR signals from arterial blood. The applied RF saturation pulses and acquisition of k-space data may be repeated for each imaging slice of the targeted volume of the subject.

Pulse sequence server 20 may then control MRI system 10 to reconstruct images from the all of the acquired k-space data. MRI system 10 may reconstruct, from arterial specific k-space data, an image that represents arterial vasculature of the subject (222). The reconstructed image of step 222 may include minimal representation of venous vasculature due to the suppressed MR signals of the venous blood. MRI system 10 may also reconstruct, from venous specific k-space data, an image that represents venous vasculature of the subject (224). The reconstructed image of step 224 may include minimal representation of arterial vasculature due to the suppressed MR signals of the arterial blood. MRI system 10, such as display 14 of workstation 12, may be configured to present the reconstructed images to a clinician for analysis and diagnosis (226).

In other examples, the acquisition of MR signals and reconstruction of k-space data may be performed using different techniques. For example, arterial and venous signals may be acquired using continuous acquisition when the saturation arterial and venous signals (e.g., blood with suppressed MR signals) flow through the imaging slice at different times. In this manner retrospective segmentation of arterial and venous signals may be used to reconstruct the various images. In any technique saturation band geometry and/or timing may be modified as needed according to the acquisition technique.

Although not described in FIG. 7, the pulse sequence generated by pulse sequence sever 20 may control MRI system 10 to apply addition saturation pulses to each of the imaging slices for selective suppression of MR signals from fat or other background artifacts. These additional saturation pulses may be applied as a part of the acquisition pulse sequence or applied separately as needed to suppress MR signals from non-targeted tissues. Alternative, or in addition to the additional saturation pulses, MRI system 10 may employ one or more image processing techniques (e.g., subtraction methods) to remove undesired background signal and/or artifacts.

Figure 8A:
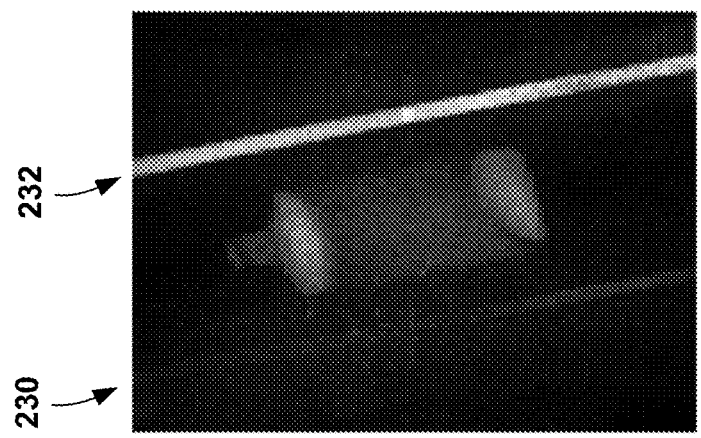
FIGS. 8A and 8B are example images of an arterial phase and a venous phase of MRAV.
Figure 8B:
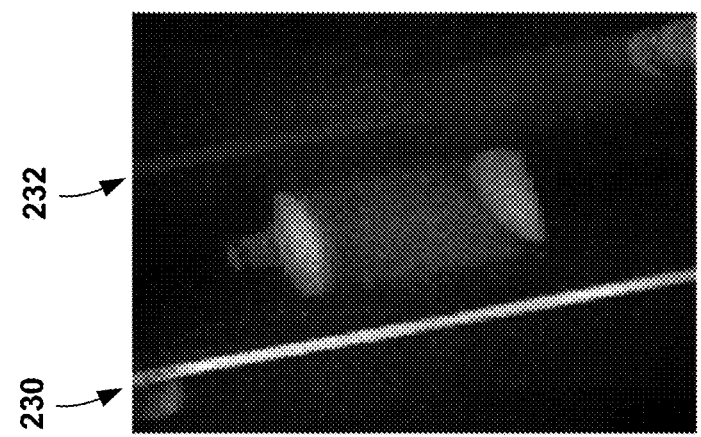

FIGS. 8A and 8B are example images acquired in a flow phantom of an arterial phase and a venous phase of MRAV. Utilizing the techniques described herein, such as the techniques described in FIG. 7, images are reconstructed to show selective representations of arterial vasculature (FIG. 8A) and venous vasculature (FIG. 8B.). The images of FIGS. 8A and 8B were reconstructed from a respective arterial specific imaging slice and venous specific imaging slice obtained within a single R-R interval.

As shown in FIG. 8A, arterial blood 230 is shown as a white line due to unsuppressed MR signals from arterial blood when the arterial specific imaging slice was acquired. In contrast, venous blood 232 is minimally noticeable due to the RF saturation pulses applied to suppress the MR signals from venous blood entering the arterial specific imaging slice.

As shown in FIG. 8B, venous blood 232 is shown as a white line due to unsuppressed MR signals from venous blood when the venous specific imaging slice was acquired. In contrast, arterial blood 230 is minimally noticeable due to the RF saturation pulses applied to suppress the MR signals from arterial blood entering the arterial specific imaging slice.

Figure 9A:
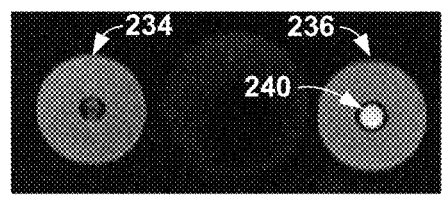
FIGS. 9A-9E are example images of steps in a subtractive image processing technique for generating representations of arterial and venous vasculature.
Figure 9B:
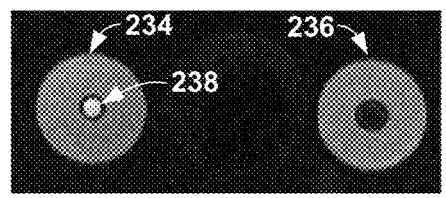
Figure 9C:
Figure 9D:
Figure 9E:
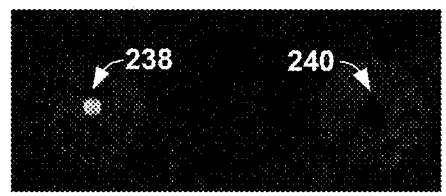
Figure 10:
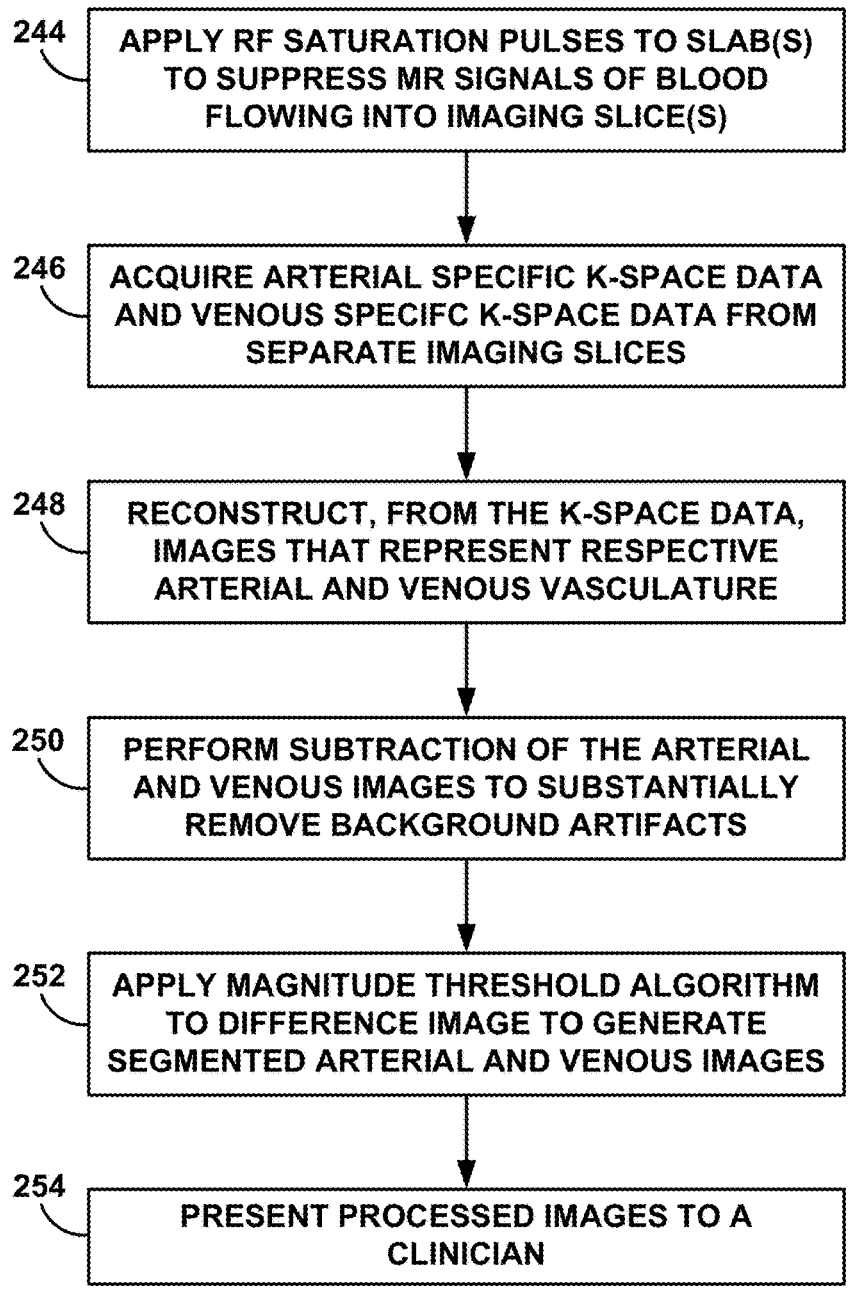
FIG. 10 is a flow diagram of an example process for generating representations of arterial and venous vasculature using a subtractive image processing technique.

FIGS. 9A-9E are example images from steps in a subtractive image processing technique for generating representations of arterial and venous vasculature. FIG. 10 is a flow diagram of an example process for generating representations of arterial and venous vasculature using the subtractive image processing technique illustrated in the images of FIGS. 9A-9E. FIGS. 9A-9E thus correspond to respective steps of the flow diagram of FIG. 10. When RF slice-encompassing saturation pulses are not applied to suppress MR signals from fat or other background tissues or motion, subtractive image processing techniques may be used to isolate signals due to arterial and venous vasculature.

Pulse sequence server 20 may be described as controlling MRI system to perform various functions with a pulse sequence. However, in other examples, different servers, processors, or systems may be configured to at least partially control MRI system 10 to perform the functions. For example, data processing server 24 or other processors may be configured to perform at least part of the image processing techniques if pulse sequence server 20 does not perform such functions.

Pulse sequence server 20 may be configured to perform a pulse sequence that controls MRI system 10 to perform various functions. MRI system 10 may be controlled to apply RF saturation pulses to one or more slabs, or bands, to suppress MR signals of blood that flows into one or more imaging slices (244). The pulse sequence may then control MRI system 10 to acquire arterial specific k-space data and venous specific k-space data from separate respective imaging slices following the application of RF excitation pulses (246). As described herein, the arterial specific k-space data may include non-suppressed MR signals from arterial blood and suppressed MR signals from venous blood. The venous specific k-space data may include non-suppressed MR signals from venous blood and suppressed MR signals from arterial blood.

Pulse sequence server 20 may then control MRI system 10 to reconstruct images from the all of the acquired k-space data. MRI system 10 may reconstruct, from arterial specific k-space data and venous specific k-space data, images that represent respective arterial and venous vasculature of the subject (248). In some examples, data processing server 24 may be configured to perform the reconstruction of the images. An example of the image of venous specific k-space data is shown in FIG. 9A. As shown in the image of FIG. 9A, cross-sections of unsuppressed background signal from stationary phantoms 234 and 236 are visible. Venous signal 240 is also shown from non-suppressed MR signals from the venous signal, but arterial signal is not visible. An example of the image of arterial specific k-space data is shown in FIG. 9B. As shown in the image of FIG. 9B, cross-sections of unsuppressed background signal from stationary phantoms 234 and 236 are visible. Arterial signal 238 is also shown from non-suppressed MR signals from the arterial signal, but venous signal is not visible.

Data processing server 24 may also perform one or more image processing algorithms on the reconstructed images to remove background signals, for example. Data processing server 24 may be configured to perform subtraction of the venous image of FIG. 9A and the arterial image of FIG. 9B to substantially remove background signal and/or artifacts (250). This subtraction technique may be possible when the background signals are substantially consistent between each of the arterial and venous images. An example of the resulting difference image is shown in FIG. 9C. In the difference image, venous blood 240 is visible as white and arterial blood 238 is visible as black against a neutral gray background.

From the difference image of FIG. 9C, data processing server 24 may apply a magnitude threshold algorithm to the difference image to generate segmented arterial and venous images (252). The image of FIG. 9D illustrates an example post-threshold venous segmentation where only venous blood 240 remains visible in the image. Arterial blood 238 is no longer visible. The image of FIG. 9E illustrates an example post-threshold arterial segmentation where only arterial blood 238 remains visible in the image. Venous blood 240 is no longer visible. In this manner, arterial and venous images may be generated without RF saturation pulses applied to suppress MR signals from background tissues or other unwanted areas of the subject. Other image processing techniques may also be used to generate the arterial and venous images. For example, phase-based techniques, or maximum/minimum intensity projection may be used to isolate the venous and arterial blood.

The disclosure also contemplates computer-readable storage media comprising instructions to cause a processor to perform any of the functions and techniques described herein. The computer-readable storage media may take the form of any volatile, non-volatile, magnetic, optical, or electrical media, such as a RAM, ROM, NVRAM, EEPROM, flash memory, or any other digital media. The computer-readable storage media may be non-transitory. A programmer, such as patient programmer or clinician programmer, or other computing device may also contain a more portable removable memory type to enable easy data transfer or offline data analysis.

The techniques described in this disclosure, including those attributed to MRI system 10, pulse sequence server 20, data processing server 24, or any other system or processor and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in one or more computing systems integrated into MRI system 10. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. For example, any of the techniques or processes described herein may be performed within one device or servers or at least partially distributed amongst two or more devices or servers via a network. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium may comprise non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described that include applying RF pulses to suppress MR signals and/or promote MR signals to acquire arterial and venous images without a single cardiac cycle. These examples include various different ordering and/or timing of pulses within a pulse sequence in order to acquire desired MR signals of arterial and/or venous blood. These and other examples are within the scope of the following claims.

What is claimed is:

1. A method comprising:
acquiring a signal indicative of a start of a cardiac cycle of a subject;
performing, by one or more processors, a pulse sequence that directs a magnetic resonance imaging (MRI) system to:
during the cardiac cycle, apply a first radio frequency (RF) saturation pulse to one slab of one or more slabs such that magnetic resonance (MR) signals indicative of blood of a second vessel that flows into a first imaging slice are suppressed;
during one of the cardiac cycle or an immediately prior cardiac cycle, apply a second RF saturation pulse to one slab of the one or more slabs such that MR signals indicative of blood of a first vessel that flows into a second imaging slice are suppressed;
during the cardiac cycle, acquire first data from the subject following the application of one or more first RF excitation pulses, wherein the first data is indicative of MR signals from blood of the first vessel and suppressed MR signals from blood of the second vessel; and
during the cardiac cycle, acquire second data from the subject following the application of one or more second RF excitation pulses, wherein the second data is indicative of MR signals from blood of the second vessel and suppressed MR signals from blood of the first vessel;
reconstructing, from the acquired first data, a first image that represents at least a portion of the first vessel the subject; and
reconstructing, from the acquired second data, a second image that represents at least a portion of the second vessel of the subject.

2. The method of claim 1,
wherein
the first RF saturation pulse is applied to a first slab of the one or more slabs such that MR signals indicative of blood of the second vessel that flows into the first imaging slice of the first data are suppressed; and
wherein the second RF saturation pulse is applied to a second slab of the one or more slabs different than the first slab such that MR signals indicative of blood of the first vessel that flows into the second imaging slice of the second data are suppressed.

3. The method of claim 2, wherein performing the pulse sequence comprises performing the pulse sequence that directs the MRI system to:
apply the first RF saturation pulse;
after application of the first RF saturation pulse, apply the second RF saturation pulse;
acquire the first data from the subject following the one or more first RF excitation pulses applied after the second RF saturation pulse; and
acquire the second data from the subject following the one or more second RF excitation pulses applied after the one or more first RF excitation pulses.

4. The method of claim 2, wherein performing the pulse sequence comprises performing the pulse sequence that directs the MRI system to:
apply the second RF saturation pulse;
after application of the second RF saturation pulse, apply the first RF saturation pulse;
acquire the first data from the subject following the one or more first RF excitation pulses applied after the first RF saturation pulse; and
acquire the second data from the subject following the one or more second RF excitation pulses applied after the one or more first RF excitation pulses.

5. The method of claim 2, wherein performing the pulse sequence comprises performing the pulse sequence that directs the MRI system to:
apply the second RF saturation pulse;
after application of the second RF saturation pulse, apply the first RF saturation pulse;
acquire the second data from the subject following the one or more second RF excitation pulses applied after the first RF saturation pulse; and
acquire the first data from the subject following the one or more first RF excitation pulses applied after the one or more second RF excitation pulses.

6. The method of claim 5, wherein performing the pulse sequence comprises performing the pulse sequence that directs the MRI system to:
apply the second RF saturation pulse during the cardiac cycle.

7. The method of claim 2, wherein performing the pulse sequence comprises performing the pulse sequence that directs the MRI system to:
apply the second RF saturation pulse;
acquire the second data from the subject following the one or more second RF excitation pulses applied after the second RF saturation pulse;
after application of the second RF excitation pulses, apply the first RF saturation pulse; and
acquire the first data from the subject following the one or more first RF excitation pulses applied after first RF saturation pulse.

8. The method of claim 1, wherein performing the pulse sequence that directs the MRI system to apply the one or more RF saturation pulse comprises performing the pulse sequence that directs the MRI system to:

apply the first and second RF saturation pulses to a single slab such that MR signals indicative of blood of the second vessel that flows into the first imaging slice of the first data are suppressed and MR signals indicative of blood of the first vessel that flows into the second imaging slice of the second data are suppressed.

9. The method of claim 8, wherein each of the first and second imaging slices is outside of the single slab.

10. The method of claim 8, wherein each of the first and second imaging slices is within the single slab.

11. The method of claim 1, wherein the application of at least one of the RF saturation pulses and the first and second RF excitation pulses are multiplexed at the respective slab or slice locations.

12. The method of claim 1, wherein
performing the pulse sequence comprises performing the pulse sequence that directs the MRI system to:
apply one or more additional RF saturation pulses to the first imaging slice such that MR signals within the first imaging slice are suppressed; and
apply one or more additional RF saturation pulses to the second imaging slice such that MR signals within the second imaging slice are suppressed.

13. The method of claim 1, wherein performing the pulse sequence comprises performing the pulse sequence that directs the MRI system to:
acquire the first data as a first single shot in coordination with the application of the one or more first RF excitation pulses; and
acquire the second data as a second single shot in coordination with the application of the one or more second RF excitation pulses.

14. The method of claim 1, wherein performing the pulse sequence comprises performing the pulse sequence that directs the MRI system to:
abstain from application of any RF pulses during a period of time between the application of the first and second RF saturation pulses and the application of the one or more first RF excitation pulses, wherein the period of time is selected such that the application of one or more first RF excitation pulses occurs during diastolic inflow of blood into the first imaging slice of the first data.

15. The method of claim 1, wherein the blood of the first vessel is arterial blood from an artery, and wherein the blood from the second vessel is venous blood from a vein.

16. A computing system comprising:
processing circuitry configured to:
acquire a signal indicative of a start of a cardiac cycle of a subject;
perform a pulse sequence that directs a magnetic resonance imaging (MRI) system to:
during the cardiac cycle, apply a first radio frequency (RF) saturation pulse to one slab of one or more slabs such that magnetic resonance (MR) signals indicative of blood of a second vessel that flows into a first imaging slice are suppressed;
during one of the cardiac cycle or an immediately prior cardiac cycle, apply a second RF saturation pulse to one slab of the one or more slabs such that MR signals indicative of blood of a first vessel that flows into a second imaging slice are suppressed;
during the cardiac cycle, acquire first data from the subject following the application of one or more first RF excitation pulses, wherein the first data is indicative of MR signals from blood of the first vessel and suppressed MR signals from blood of the second vessel; and during the cardiac cycle, acquire second data from the subject following the application of one or more second RF excitation pulses, wherein the second data is indicative of MR signals from blood of the second vessel and suppressed MR signals from blood of the first vessel;
reconstruct, from the acquired first data, a first image that represents at least a portion of the first vessel of the subject; and
reconstruct, from the acquired second data, a second image that represents at least a portion of the second vessel of the subject.

17. The computing system of claim 16,
wherein the first RF saturation pulse is applied to a first slab of the one or more slabs such that MR signals indicative of blood of the second vessel that flows into the first imaging slice of the first data are suppressed; and
wherein the second RF saturation pulse is applied to a second slab of the one or more slabs different than the first slab such that MR signals indicative of blood of the first vessel that flows into the second imaging slice of the second data are suppressed.

18. The computing system of claim 17, wherein the processing circuitry is configured to perform the pulse sequence that directs the MRI system to:
apply the first RF saturation pulse;
after application of the first RF saturation pulse, apply the second RF saturation pulse;
acquire the first data from the subject following the one or more first RF excitation pulses applied after the second RF saturation pulse; and
acquire the second data from the subject following the one or more second RF excitation pulses applied after the one or more first RF excitation pulses.

19. The computing system of claim 17, wherein the processing circuitry is configured to perform the pulse sequence that directs the MRI system to:
apply the second RF saturation pulse;
after application of the second RF saturation pulse, apply the first RF saturation pulse;
acquire the second data from the subject following the one or more second RF excitation pulses applied after the first RF saturation pulse; and
acquire the first data from the subject following the one or more first RF excitation pulses applied after the one or more second RF excitation pulses.

20. The computing system of claim 17, wherein the processing circuitry is configured to perform the pulse sequence that directs the MRI system to:
apply the second RF saturation pulse;
acquire the second data from the subject following the one or more second RF excitation pulses applied after the second RF saturation pulse;
after application of the second RF excitation pulses, apply the first RF saturation pulse; and
acquire the first data from the subject following the one or more first RF excitation pulses applied after first RF saturation pulse.

21. The computing system of claim 16, wherein the processing circuitry is configured to perform the pulse sequence that directs the MRI system to:
abstain from application of any RF pulses during a period of time between the application of the first and second RF saturation pulses and the application of the one or more first RF excitation pulses, wherein the period of time is selected such that the application of one or more first RF excitation pulses occurs during diastolic inflow of blood into the first imaging slice of the first data;

acquire the first data as a first single shot in coordination with the application of the one or more first RF excitation pulses; and acquire the second data as a second single shot in coordination with the application of the one or more second RF excitation pulses.

22. A non-transitory computer-readable storage medium comprising instructions that cause one or more processors to:

acquire a signal indicative of a start of a cardiac cycle of a subject;

perform a pulse sequence that directs a magnetic resonance imaging (MRI) system to:

during the cardiac cycle, apply a first radio frequency (RF) saturation pulse to one slab of one or more slabs such that magnetic resonance (MR) signals indicative of blood of a second vessel that flows into a first imaging slice are suppressed;

during one of the cardiac cycle or an immediately prior cardiac cycle, apply a second RF saturation pulse to one slab of the one or more slabs such that MR signals indicative of blood of a first vessel that flows into a second imaging slice are suppressed;

during the cardiac cycle, acquire first data from the subject following the application of one or more first RF excitation pulses, wherein the first data is indicative of MR signals from blood of the first vessel and suppressed MR signals from blood of the second vessel; and during the cardiac cycle, acquire second data from the subject following the application of one or more second RF excitation pulses, wherein the second data is indicative of MR signals from blood of the second vessel and suppressed MR signals from blood of the first vessel;

reconstruct, from the acquired first data, a first image that represents at least a portion of the first vessel of the subject; and reconstruct, from the acquired second data, a second image that represents at least a portion of the second vessel of the subject.

* * * * *